United States Patent
Yuan et al.

(10) Patent No.: US 9,303,208 B2
(45) Date of Patent: Apr. 5, 2016

(54) LIQUID CRYSTAL COMPOUND CONTAINING CYCLOPENTYL AND DIFLUOROMETHENEOXY LINKING GROUP, PREPARATION METHOD AND APPLICATION THEREOF

(71) Applicant: Shijiazhuang Chengzhi Yonghua Display Materials Co., Ltd., Shijiazhuang (CN)

(72) Inventors: Guoliang Yuan, Shijiazhuang (CN); Zhian Liang, Shijiazhuang (CN); Kui Wang, Shijiazhuang (CN); Ruimao Hua, Shijiazhuang (CN); Gang Wen, Shijiazhuang (CN); Miaofang Zhang, Shijiazhuang (CN); Jinsong Meng, Shijiazhuang (CN)

(73) Assignee: SHIJIAZHUANG CHENGZHI YONGHUA DISPLAY MATERIALS CO., LTD., Shijiazhuang (CN)

( * ) Notice: Subject to any disclaimer, the term of this patent is extended or adjusted under 35 U.S.C. 154(b) by 0 days.

(21) Appl. No.: 14/388,676

(22) PCT Filed: Jan. 18, 2013

(86) PCT No.: PCT/CN2013/000056
§ 371 (c)(1),
(2) Date: Sep. 26, 2014

(87) PCT Pub. No.: WO2013/143344
PCT Pub. Date: Oct. 3, 2013

(65) Prior Publication Data
US 2015/0218449 A1    Aug. 6, 2015

(30) Foreign Application Priority Data
Mar. 27, 2012 (CN) .......................... 2012 1 0083535

(51) Int. Cl.
*C07C 43/20* (2006.01)
*C07C 43/205* (2006.01)
*C07C 43/21* (2006.01)
*C07C 43/225* (2006.01)
*C09K 19/30* (2006.01)

(52) U.S. Cl.
CPC ............. *C09K 19/3003* (2013.01); *C09K 19/30* (2013.01); *C09K 2019/3009* (2013.01)

(58) Field of Classification Search
CPC ............... C09K 19/30; C09K 19/3003; C09K 2019/3009; C07C 43/20; C07C 43/205; C07C 43/21; C07C 43/225
See application file for complete search history.

(56) References Cited

U.S. PATENT DOCUMENTS 7,767,277 B2 *  8/2010  Lietzau et al. ................. 428/1.1
8,211,513 B2     7/2012  Jansen et al.

FOREIGN PATENT DOCUMENTS

| CN | 1168365   | 12/1997 |
|----|-----------|---------|
| CN | 102199139 | 9/2011  |
| EP | 0789067   | 8/1997  |

OTHER PUBLICATIONS

English abstract for EP0789067; published on Aug. 3, 1997.
English abstract for CN1168365; published on Dec. 24, 1997.
English abstract for CN102199139; published on Sep. 28, 2011.

* cited by examiner

*Primary Examiner* — Yong Chu
(74) *Attorney, Agent, or Firm* — Buchanan Ingersoll & Rooney PC

(57) ABSTRACT

This invention relates to liquid crystal compounds of formula I containing cyclopentyl group and difluoromethyleneoxy linking group. Liquid crystal compounds of formula I have a large dielectric anisotropy, high clearing points, and a fast response speed, thereby having great significance to formulate a liquid crystal mixture.

formula I

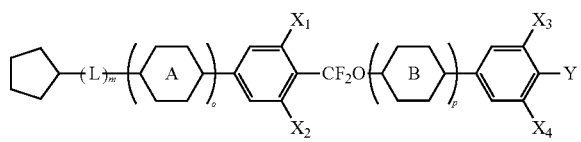

3 Claims, No Drawings

LIQUID CRYSTAL COMPOUND CONTAINING CYCLOPENTYL AND DIFLUOROMETHENEOXY LINKING GROUP, PREPARATION METHOD AND APPLICATION THEREOF

CROSS-REFERENCE TO RELATED APPLICATIONS

This application is a U.S. national phase application of PCT/CN2013/000056, filed on Jan. 18, 2013, which claims priority to Chinese Patent Application No. 201210083535.0, filed Mar. 27, 2012. The disclosure of which are herein incorporated by reference in their entirety.

TECHNICAL FIELD

This invention relates to the field of liquid crystal compounds and application, particularly relates to liquid crystal compounds containing a cyclopentyl group and difluoromethyleneoxy linking group, and their preparation method and application.

TECHNICAL BACKGROUND

Currently the liquid crystal compounds are widely applied in various types of displays, electro-optical devices, sensors and the like. Among the large number of liquid crystal compounds used in display area, the nematic liquid crystal is most widely used. Nematic liquid crystals have been used in passive TN, STN matrix display and TFT active matrix system.

Although the technology of thin-film-transistor liquid-crystal display (TFT-LCD) has been mature, it should be continuously improved to decrease the response time, to widen the phase transition temperature, to decrease the driving voltage, etc. It has been well-known that liquid crystals play an important role to improve the characteristics of LCDs. The liquid crystal compounds are required to have high chemical and thermal stability, as well as high stability in electric field and electromagnetic radiation. The liquid crystal compounds used in TFT-LCD not only should be stable to heat, UV light, electric field, and electromagnetic radiation, but also have the wide temperature range of a nematic phase, appropriate optical anisotropy, very high resistance, high voltage holding ratio, and low vapor pressure.

For dynamic picture display such as LCD-TV, in order to improve the characteristics of the device to reduce the picture motion blur and trailing, it is desired that the liquid crystal mixtures have appropriate physical properties with a short response time, a low viscosity ($\gamma 1$), and a low driving voltage. Also it is great significance to elevate the dielectric anisotropy ($\Delta \in$) of the liquid crystal compound for the modulation of liquid crystal mixture.

A large number of studies have shown that a introduction of difluoroethylene methoxy group (—$CF_2O$—) into a liquid crystal molecules will reduce rotational viscosity $\gamma 1$. In addition, due to the contribution of dipole moment of difluoromethyleneoxy bridge (—$CF_2O$—), the dipole moment of the terminal fluorine group also increases to some extent, so that the dielectric anisotropy $\Delta \in$ of the liquid crystal molecules increases. Merck of Germany and Chisso of Japan have reported several liquid crystal compounds containing various substituent and difluoromethyleneoxy group (—$CF_2O$—) (CN1717468A, CN101143808A, CN101157862A). However the introduction of difluoromethyleneoxy bridge (—$CF_2O$—) will reduce clearing point of the liquid crystal. When the liquid crystal mixture is modulated, monomer having higher melting point and higher viscosity is needed for balancing the reduction of clearing point. thus limiting the improvement of response speed of the liquid crystal mixture.

DISCLOSURE OF THE INVENTION

The objective of the present invention is to provide a liquid crystal compound having a cyclopentyl group and difluoromethyleneoxy bridge (—$CF_2O$—) and its preparation method and application.

This invention relates to liquid crystal compounds containing cyclopentyl group and difluoromethyleneoxy bridge, their general structural formula shown in formula I.

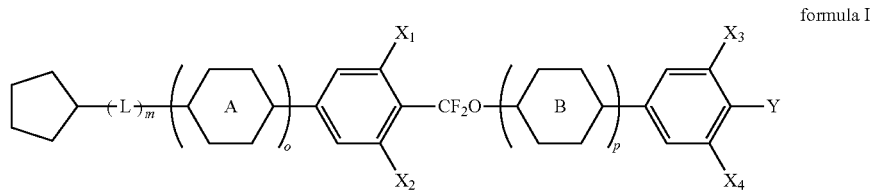

formula I

In which,

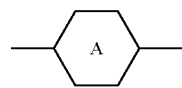

is selected from 1,4-cyclohexenylene, 1,4-phenylene or 1,4-phenylene which may be monosubstituted or polysubstituted by fluorine;

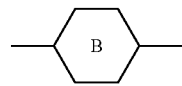

is selected from 1,4-phenylene or 1,4-phenylene, which may be monosubstituted or polysubstituted by fluorine;

L is selected from $CH_2$ or O, and $(L)_m$, is up to one oxygen atom, m is an integer of 0-6; o is 0, 1 or 2; p is 0 or 1;

$X_1$, $X_2$, $X_3$ and $X_4$ are selected from H and F;

Y is selected from H, F, Cl, —$CF_3$, —$CHF_2$, —$OCF_3$, or —$OCHF_2$.

Specifically, m is an integer of 0-5 or an integer of 0-4, or an integer of 0-3, or an integer of 0-2, or integer 0 or 1 or 2 or 3 or 4 or 5 or 6, or an integer of 1-6, or an integer of 2-5, or an integer of 3-4, or an integer of 1-5, or an integer of 1-4, or an integer of 1-3, or an integer of 2-6, or an integer of 2-5, or an integer of 2-4;

Preferably, said compound of formula I is the compound of formula II, formula II

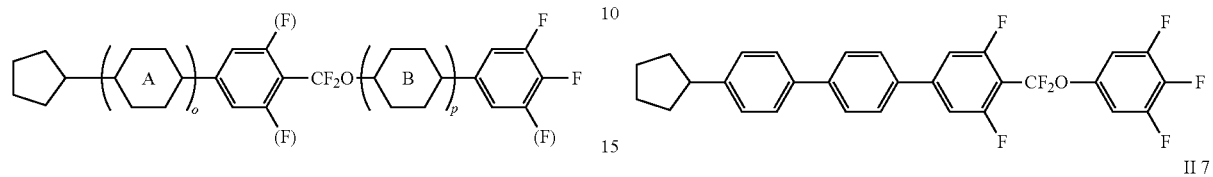

In which,

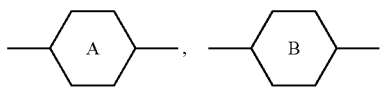

and p are as defined in claim 1; o is 1 or 2, —(F) is F or H;

Said compounds of the formula II may be at least one compound selected from formula II 1 to formula II 13.

II 1

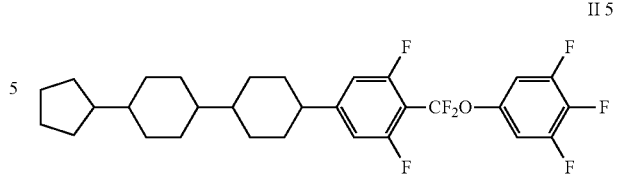

II 2

II 3

II 4

II 5

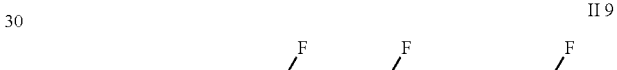

II 6

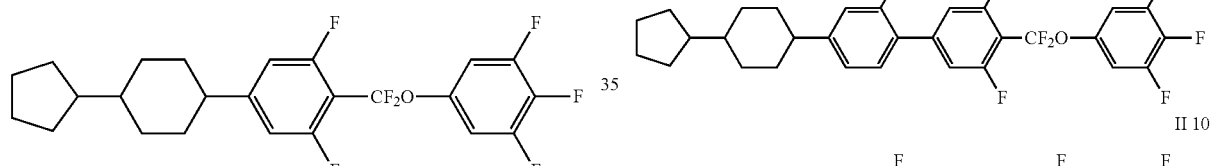

II 7

II 8

II 9

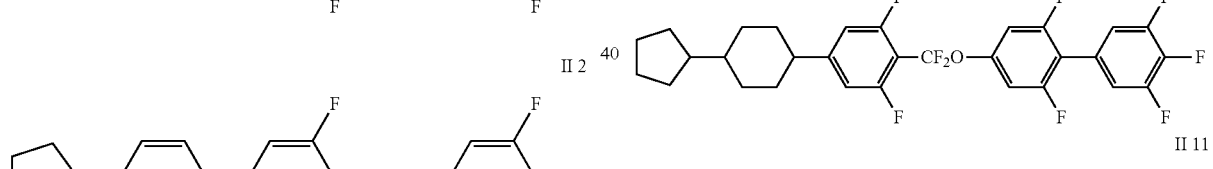

II 10

II 11

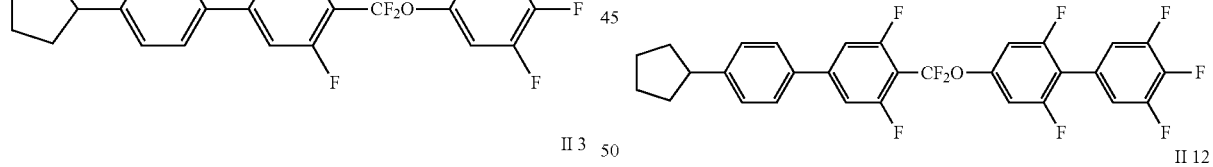

II 12

II 13

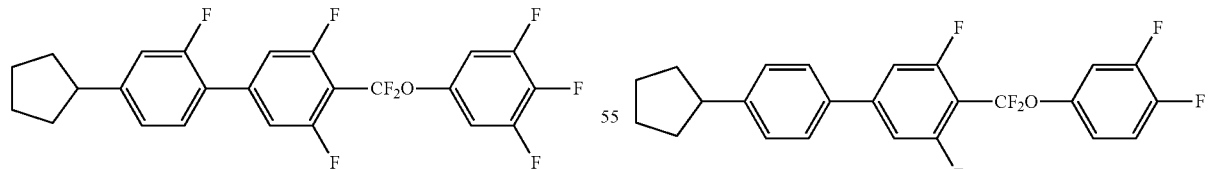

Compound of formula I was synthesized by one of the following six synthetic methods.

Wherein the compound of formula I was prepared in said method 1, in which cyclopentyl group is linked by 1,4-cyclohexylene, o is 1 or 2 and m is 0, comprising the steps of:

Method 1

Step 1: Cyclopentyl triphenyl phosphonium bromide reacted with potassium t-butoxide to give ylide reagent, which was allowed to react with 1,4-cyclohexanedione monoethylene acetal or 4,4-dicyclohexanedione monoethylene acetal to afford

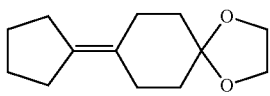 [SMILES: C1CCC(=C2CCC3(CC2)OCCO3)C1]

or

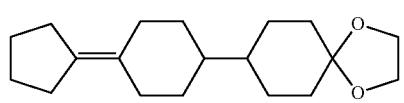 [SMILES: C1CCC(=C2CCC(C3CCC4(CC3)OCCO4)CC2)C1]

Step 2:

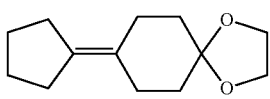 [SMILES: C1CCC(=C2CCC3(CC2)OCCO3)C1]

or

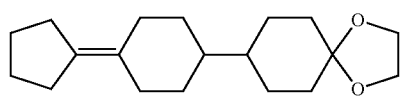

obtained in step 1 of synthetic method 1 was hydrogenated in Raney nickel catalyst to give

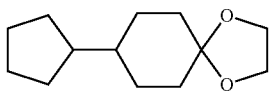 [SMILES: C1CCC(C2CCC3(CC2)OCCO3)C1]

or

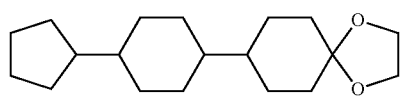

Step 3: Hydration of

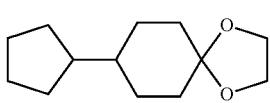

or

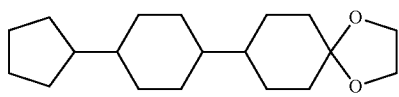

obtained in step 2 of synthetic method 1 under the conditions of pH 1-6 produced

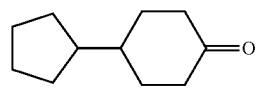

or

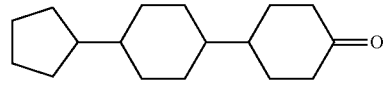 [SMILES: O=C1CCC(C2CCC(C3CCCC3)CC2)CC1]

Step 4:

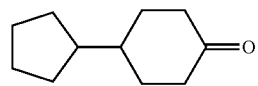 [SMILES: O=C1CCC(C2CCCC2)CC1]

or

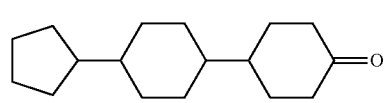 [SMILES: O=C1CCC(C2CCC(C3CCCC3)CC2)CC1]

obtained in step 3 of synthetic method 1 was allowed to react with

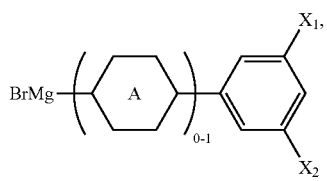

and then was dehydrated to give

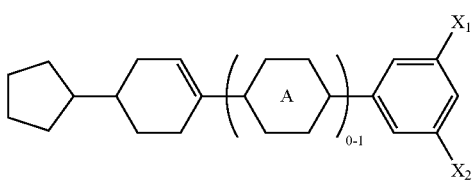

or

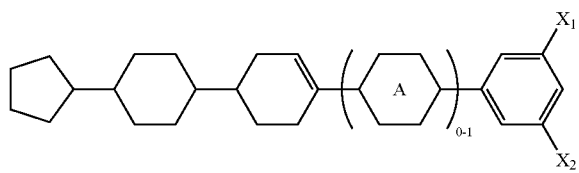

Step 5:

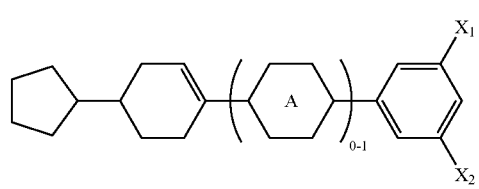

or

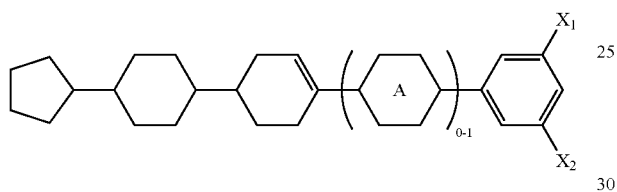

obtained in step 4 of synthetic method 1 was hydrogenated in Raney nickel catalyst to give

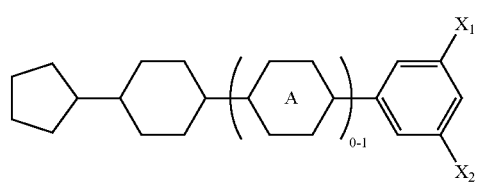

or

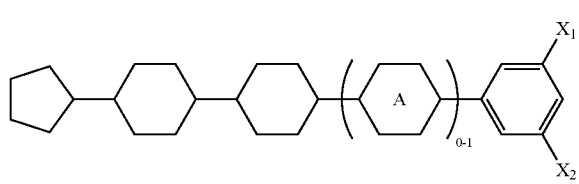

Step 6:

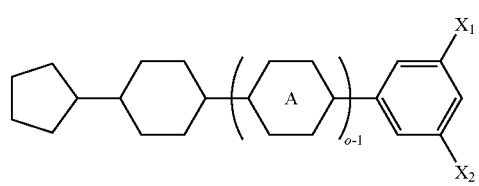

obtained in step 5 of synthetic method 1 was allowed to react with n-butyl lithium and difluorodibromomethane to afford

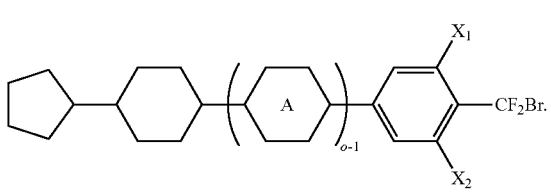

Step 7: The reaction of

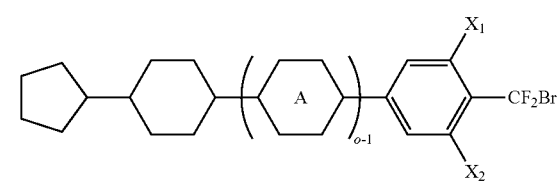

obtained in step 6 of synthetic method 1 with

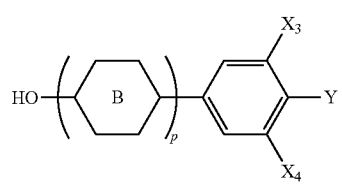

in the presence of carbonate gave compound of formula I, in which cyclopentyl group is linked by 1,4-cyclohexylene, o is 1 or 2 and m is 0.

The compound of formula I prepared in said method 2, in which

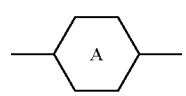

is selected from 1,4-phenylene or 1,4-phenylene which may be monosubstituted or polysubstituted by fluorine, o is 1 or 2 and m is 0, comprising the steps of:

Method 2

Step 1:

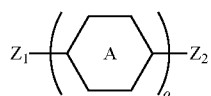

was allowed to react with n-butyl lithium to give

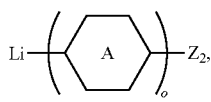

and then

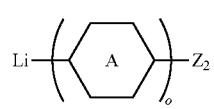

reacted with

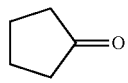

(cyclopentanone). The obtained product was dehydrated in the presence of p-toluenesulfonic acid as catalyst to give

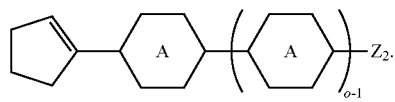

Step 2: The reaction of

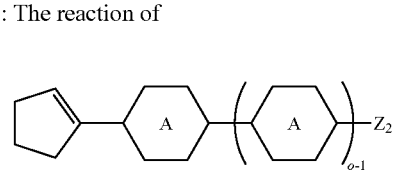

obtained in step 1 of synthetic method 2 with

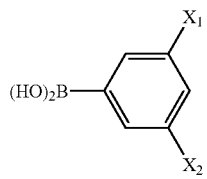

in the presence of carbonate and tetrakis(triphenylphosphine)-palladium under reflux afforded

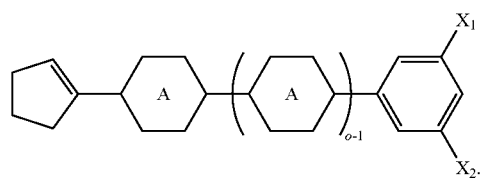

Step 3:

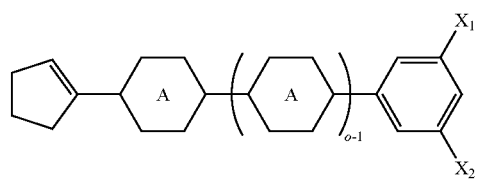

obtained in step 2 of synthetic method 2 was hydrogenated in Raney nickel catalyst to give

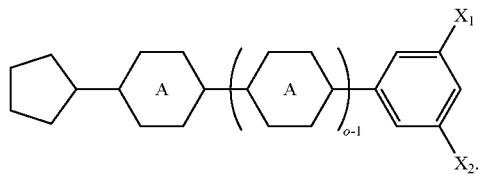

Step 4:

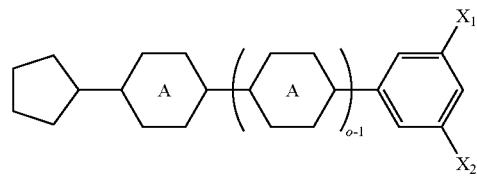

obtained in step 3 of synthetic method 2 was allowed to react with n-butyl lithium and difluorodibromomethane to give

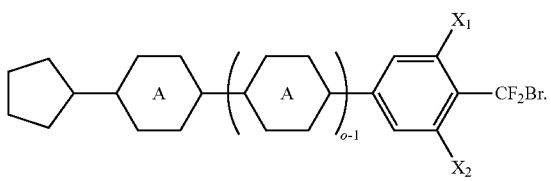

Step 5: The reaction of

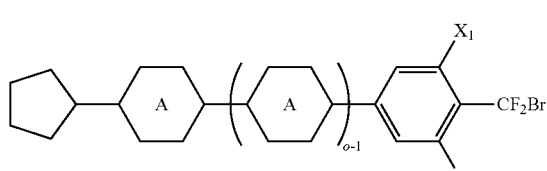

obtained in step 4 of synthetic method 2 with

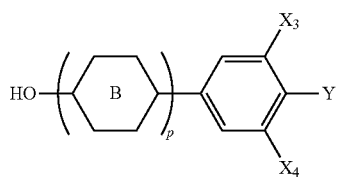

in the presence of carbonate gave compound of formula I, in which

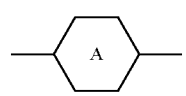

is selected from 1,4-phenylene or 1,4-phenylene which may be monosubstituted or polysubstituted by fluorine, o is 1 or 2 and m is 0.

The compound of formula I prepared in said method 3 in which $(L)_m$ is linked by

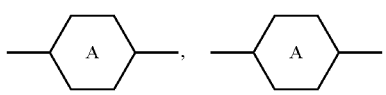

is selected from 1,4-cyclohexenylene, o is 1 or 2 and m is an integer of 1-6, comprising the steps of:

Method 3

Step 1:

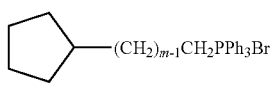

reacted with potassium t-butoxide to give glide reagent, which was allowed to react with

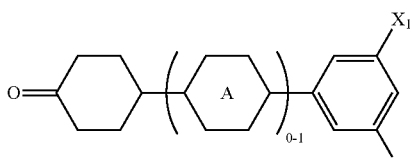

to give

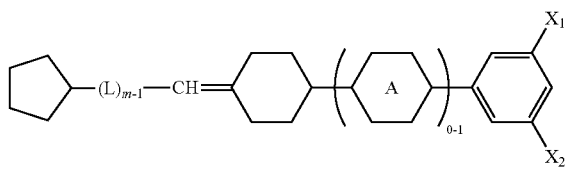

Step 2:

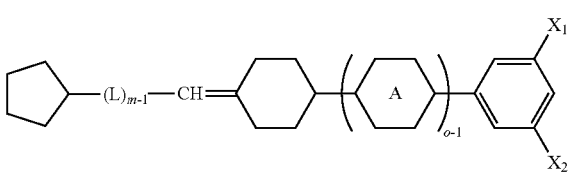

obtained in step 1 of synthetic method 3 was hydrogenated in Raney nickel catalyst to give

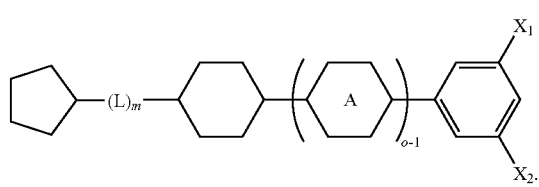

Step 3:

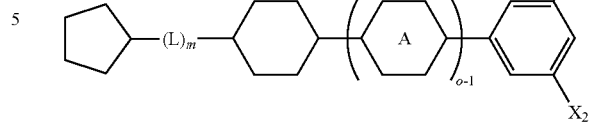

obtained in step 2 of synthetic method 3 was allowed to react with n-butyl lithium and difluorodibromomethane to give

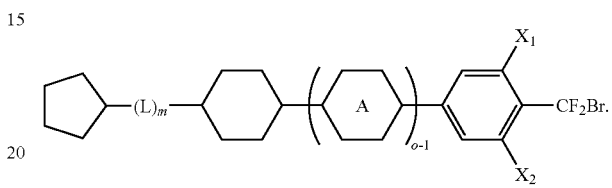

Step 4: The reaction of

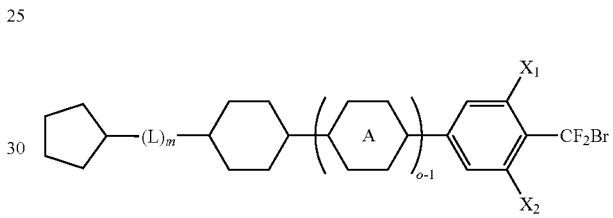

obtained in step 3 of synthetic method 3 with

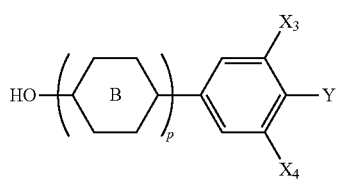

in the presence of carbonate afforded compound of formula I in which

is selected from 1,4-cyclohexenylene, o is 1 or 2 and m is an integer of 1-6.

The compound of formula I prepared in said method 4 in which $(L)_m$ is linked by

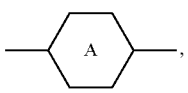

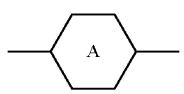

is selected from 1,4-phenylene or 1,4-phenylene which may be monosubstituted or polysubstituted by fluorine, m is an integer of 1-6, o is an integer of 0-2, comprising the steps of:

Method 4

Step 1:

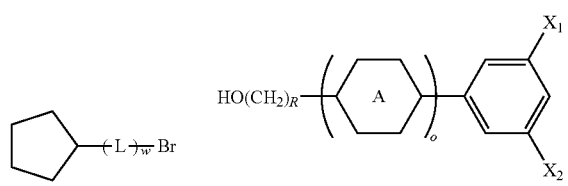

reacted with sodium hydride to give

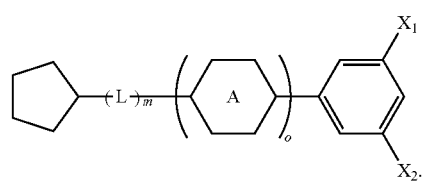

Step 2:

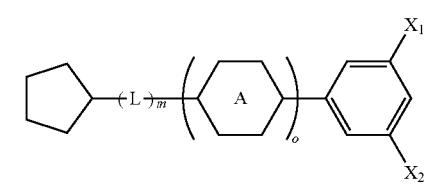

was allowed to react with n-butyl lithium and difluorodibromomethane to give

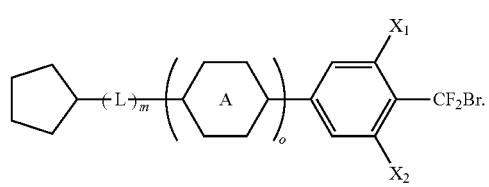

Step 3: The reaction of

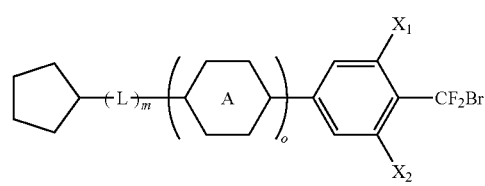

obtained in step 1 of synthetic method 4 with

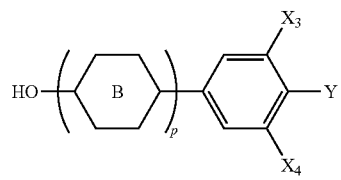

in the presence of carbonate afforded compound of formula I in which $(L)_m$ is linked by

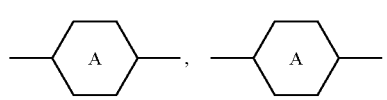

is selected from 1,4-phenylene or 1,4-phenylene which may be monosubstituted or polysubstituted by fluorine, m is an integer of-1-6, o is an integer of 0-2.

The compound of formula I prepared in method 5 in which $(L)_m$ is linked by

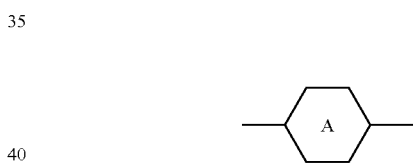

is selected from 1,4-phenylene or 1,4-phenylene which may be monosubstituted or polysubstituted by fluorine, m is an integer of 2-6, o is an integer of 0-2, and L is $CH_2$, comprising the steps of:

Method 5

Step 1:

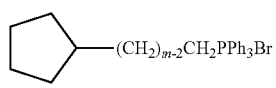

reacted with potassium t-butoxide to afford ylide reagent

Method 6

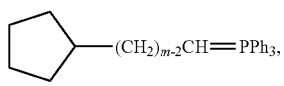

which was allowed to react with

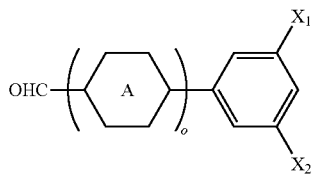

to give

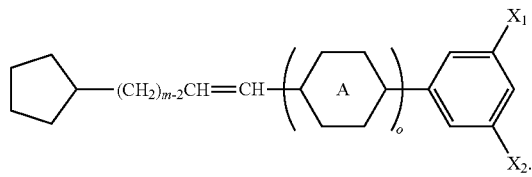

Step 2:

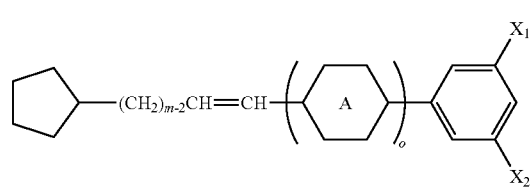

obtained in step 1 of synthetic method 5 was hydrogenated in Raney nickel catalyst to give

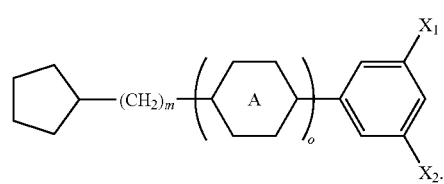

Step 3: The reaction of

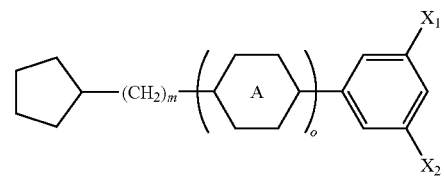

obtained in step 2 of synthetic method 5 with n-butyl lithium and difluorodibromomethane gave

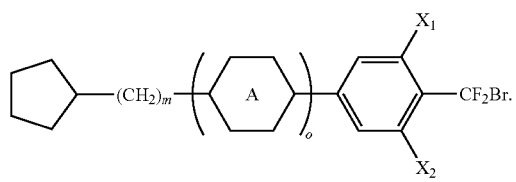

Step 4: The reaction of

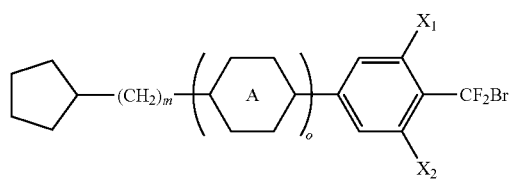

obtained in step 3 of synthetic method 5 with

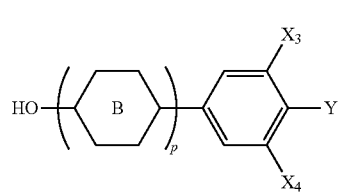

in the presence of carbonate afforded compound of formula I in which $(L)_m$ is linked by

which selected from 1,4-phenylene or 1,4-phenylene which may be monosubstituted or polysubstituted by fluorine, m is an integer of 2-6, o is an integer of 0-2, L is $CH_2$.

The compound of formula I prepared in method 6, in which $(L)_m$ is linked by

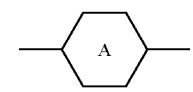

is selected from 1,4-phenylene or 1,4-phenylene which may be monosubstituted or polysubstituted by fluorine, m is an 1, o is an integer of 0-2, and L is $CH_2$, comprising the steps of:

Step 1: The reaction of

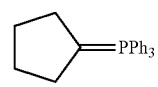

with

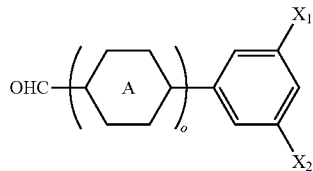

afforded

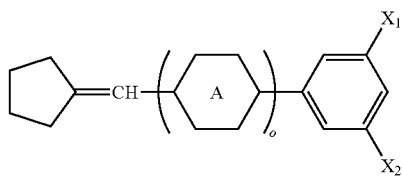

Step 2:

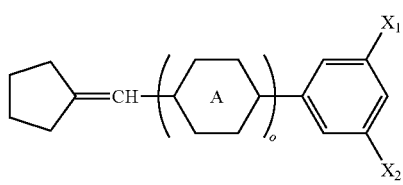

obtained in step 2 of synthetic method 6 was enated in Raney nickel catalyst to give

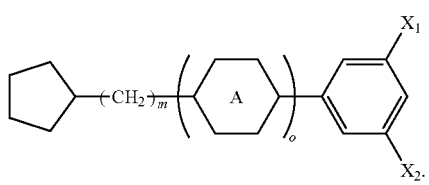

Step 3: The reaction of

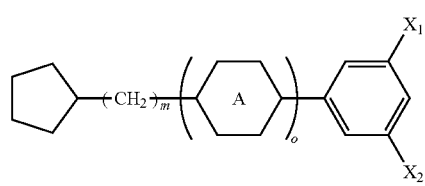

obtained in step 2 of synthetic method 6 with n-butyl lithium and difluorodibromomethane gave

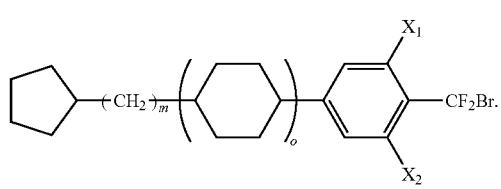

Step 4: The reaction of

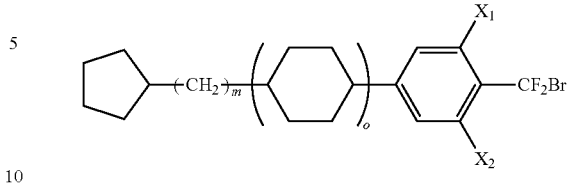

obtained in step 3 of synthetic method 6 with

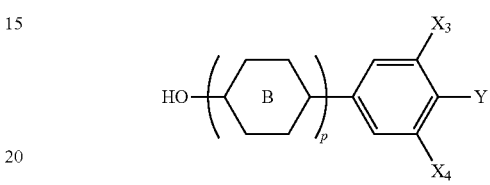

in the presence of carbonate gave compound of formula I in which $(L)_m$ is linked by

which selected from 1,4-phenylene or 1,4-phenylene which may be monosubstituted or polysubstituted by fluorine, m is 1, o is an integer of 0-2, L is $CH_2$.

The above methods, said

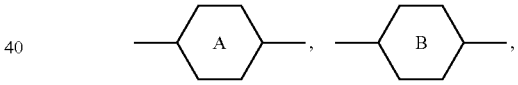

o, p, L, m, $X_1$, $X_2$, $X_3$, $X_4$ and Y are as defined in claim 1: said Z1 and Z2 are selected from the at least one bromine and iodine; W are selected from an integer of 0-4, R are selected from an integer of 0 to 4, and W+R=m−1.

In step 1 of synthetic method 1, the molar ratio of cyclopentyl triphenyl phosphonium bromide:potassium t-butoxide:1,4-cyclohexanedione monoethylene acetal or 4,4-dicyclohexanedione monoethylene acetal is 1~2:1~2:1, preferably 1.2:1.2:1. Said the reaction of cyclopentyl triphenyl phosphonium bromide and potassium t-butoxide, the reaction temperature is of −15~10° C., preferably is −10° C.; the reaction time is 0.5~2 hours, preferably is 1 hour; In the olefination step, the reaction temperature is −15~10° C., preferably is 0° C., the reaction time is 1~10 hours, preferably is 3 hours.

In the step 2 of synthetic method 1, the ratio between

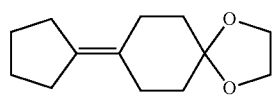 [SMILES: C1CCC(=C2CCC3(CC2)OCCO3)C1]

or

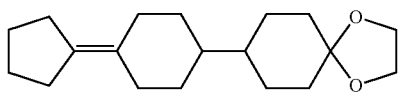

and Raney nickel catalyst is 100:5-35 by weight, preferably is 100:20. In step 2 of synthetic method 1, the reaction temperature is 0~100° C., preferably is 30° C., the reaction time is 1~10 hours, preferably is 6 hours.

In step 3 of synthetic method 1, the reaction temperature is 0~110° C., preferably is 30° C., the reaction time is 5~35 hours, preferably is 20 hours.

In step 4 of synthetic method 1, the molar ratio between

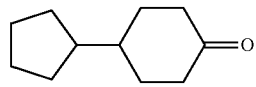

or

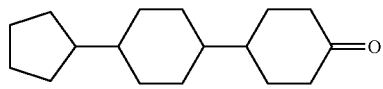 [SMILES: O=C1CCC(C2CCC(C3CCCC3)CC2)CC1]

and

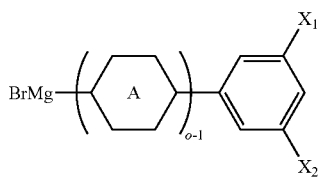

is 1:0.9~1.2, preferably is 1:1; the reaction temperature is 0~70° C., preferably is 30° C.; the reaction time is 0.5~3 hours, preferably is 1.5 hours.

In the step 5 of synthetic method 1, the ratio between

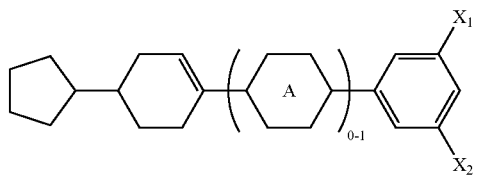

or

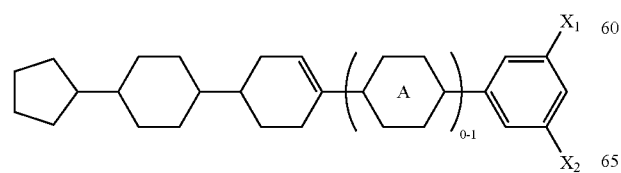

and Raney nickel catalyst is 100:5~35 by weight, specifically is 100~20. The hydrogenation reaction temperature is 0~100° C., preferably is 30° C.; the reaction time is 1-10 hours, preferably is 6 hours.

In step 6 of synthetic method 1, the molar ratio of

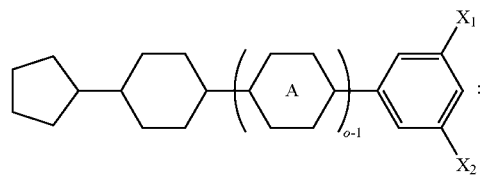

n-butyl lithium:difluorodibromomethane is 1:1~1.3:1~1.6, preferably is 1:1.1:1.2. The reaction temperature is −100~50° C., preferably is −60° C.; the reaction time is 0.5~4 hours, preferably is 2 hours.

In step 7 of synthetic method 1, said carbonate is selected from sodium carbonate or potassium carbonate; the molar ratio of

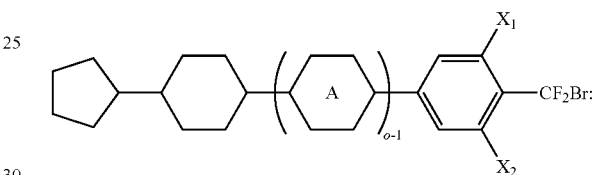

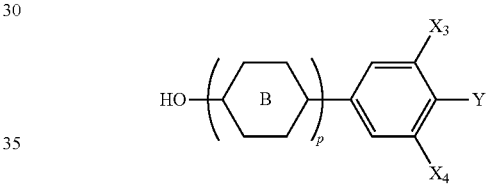

is 1:1~1.5, preferably is 1:1.2;

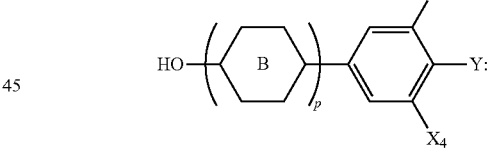

carbonate is 1:1~3, preferably is 1:2; the reaction temperature is 30~100° C., preferably is 60° C., the reaction time is 2~4 hours, preferably is 3 hours.

In step 1 of synthetic method 2, the molar ratio of

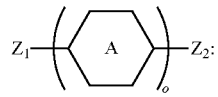

n-butyl lithium:

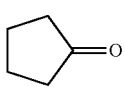

(cyclopentanone) is 1:0.9~1.2:0.9~1.4, specifically is 1:1:1. In reaction of

with n-butyl lithium, the reaction temperature is −60 to −100° C., preferably is −80° C., the reaction time is 0.1~1 hours, preferably is 0.5 hour. In reaction of

with

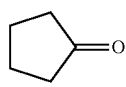

(cyclopentanone), the reaction temperature is −60 to −100° C., preferably is −80° C.; the reaction time is 0.5~4 hours, preferably is 2 hours.

In step 2 of synthetic method 2, Said carbonate is selected from sodium carbonate or potassium carbonate; the molar ratio of

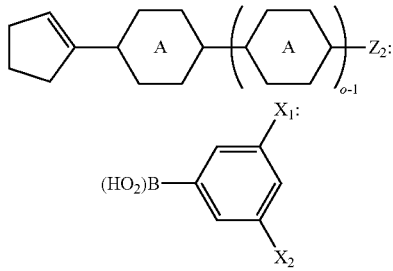

carbonate:tetrakis(triphenylphosphine)palladium is 1:1~1.3: 1~2:0.002~0.02, preferably is 1:1.1:1.2:0.0075; reflux time is 3~8 hours, preferably is 5 hours.

In the step 3 of synthetic method 2, the ratio between

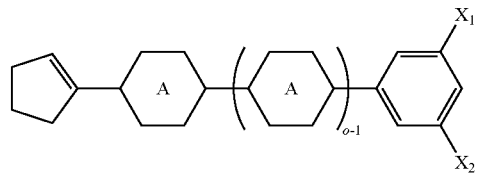

and Raney nickel catalyst is 100:5~35 by weight, preferably is 100:20; the reaction temperature is 0~100° C., preferably is 30° C.; the reaction time is 1~10 hours, preferably is 6 hours.

In step 4 of synthetic method 2, the molar ratio of

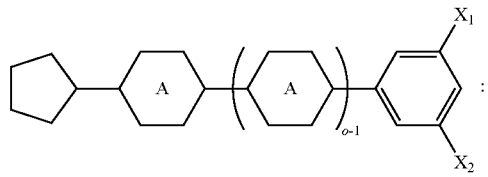

n-butyl lithium:difluorodibromomethane is 1:1-1.3:1-1.6, preferably is 1:1.1:1.2; the reaction temperature is −100 to −50° C., preferably is −60° C.; the reaction time is 0.5-4 hours, preferably is 2 hours.

In step 5 of synthetic method 2, Said carbonate is selected from sodium carbonate or potassium carbonate; the molar ratio of

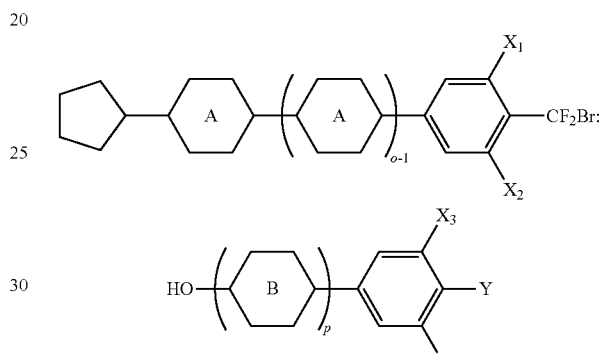

is 1:1-1.5, specifically is 1:1.2;

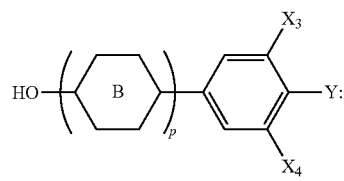

carbonate is 1:1~3, preferably is 1:2; the reaction temperature is 30~100° C., preferably is 60° C.; the reaction time is 2~4 hours, preferably is 3 hour.

In step 1 of synthetic method 3, the molar ratio of

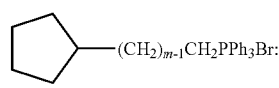

potassium t-butoxide:

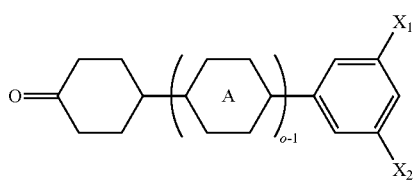

is 1~2:1~2:1, preferably is 1.2:1.2:1; In the reaction of

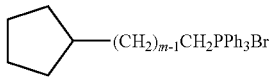

with potassium t-butoxide, the reaction temperature is −15~10° C., preferably is 10° C.; the reaction time is 0.5~2 hours, preferably is 1 hour. In the olefination step, the reaction temperature is −15~10° C., preferably is 0° C.; the reaction time is 1~10 hours, preferably is 3 hours.

In the step 2 of synthetic method 3, the ratio between

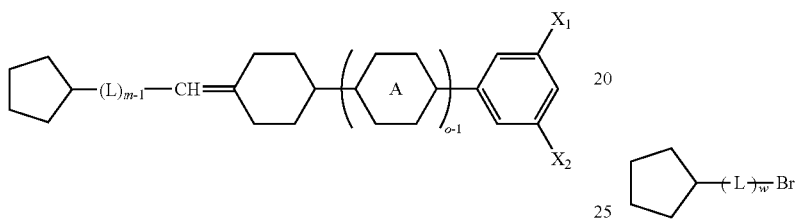

and Raney nickel catalyst is 100:5-35 by weight, preferably is 100:20; the reaction temperature is 0~100° C., preferably is 30° C.; the reaction time is 1~10 hours, preferably is 6 hours.

In step 3 of synthetic method 3, the molar ratio of

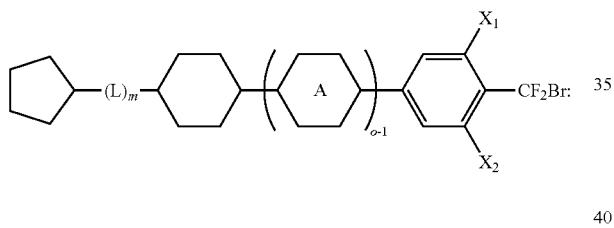

n-butyl lithium:difluorodibromomethane is 1:1-1.3:1-1.6, preferably is 1:1.1:1.2; the reaction temperature is −100 to −50° C., preferably is −60° C.; the reaction time is 0.5~4 hours, preferably is 2 hours.

In step 4 of synthetic method 3, the molar ratio of

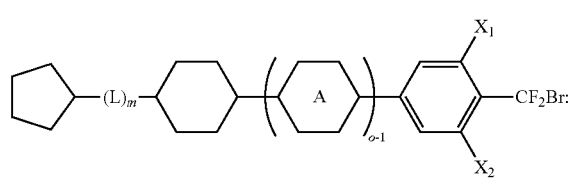

:

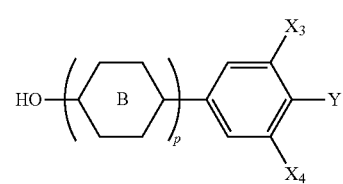

is 1:1-1.5, preferably is 1:1.2;

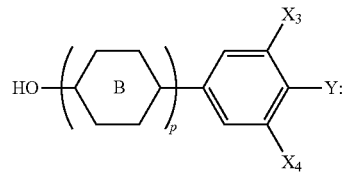

carbonate is 1:1~2, preferably is 1:2; the reaction temperature is 30~100° C., preferably is 60° C.; the reaction time is 2~4 hours, preferably is 3 hours.

In step 1 of synthetic method 4, the molar ratio of

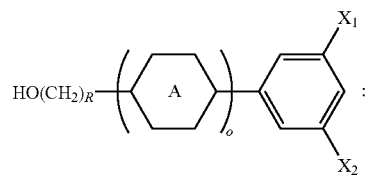

NaH is 1:1~1.3:1~1.6, preferably is 1:1:1.2; the reaction temperature is 0~60° C., preferably is 30° C.; the reaction time is 18~22 hours, preferably is 20 hours.

In step 2 of synthetic method 4, the molar ratio of

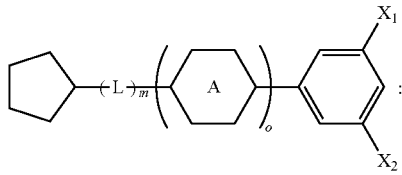

n-butyl lithium:difluorodibromomethane is 1:1~1.3:1~1.6, preferably is 1:1.1:1.2; the reaction temperature is −100 to −50° C., preferably is −60° C.; the reaction time is 0.5~4 hours, preferably is 2 hours.

In step 3 of synthetic method 4, said carbonate is selected from sodium carbonate or potassium carbonate; the molar ratio of

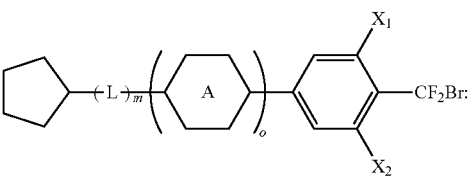

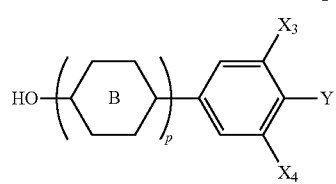

is 1:1~1.5, preferably is 1:1.2;

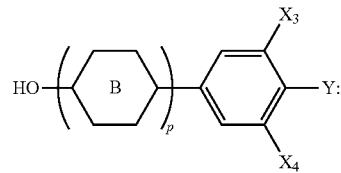

carbonate is 1:1~2; the reaction temperature is 30~100° C., preferably is 60° C.; the reaction time is 2~4 hours, preferably is 3 hours.

In step 1 of synthetic method 5, the molar ratio of

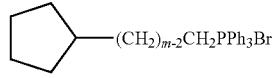

potassium t-butoxide:

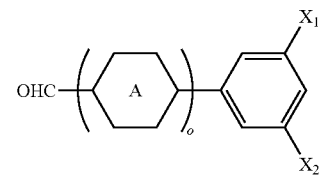

is 1.1~1.3:1.1~1.3:1, preferably is 1.2:1.2:1. In the reaction of

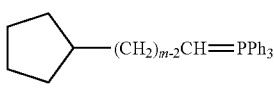

with potassium t-butoxide, the reaction temperature is −20~10° C., preferably is −5° C.; the reaction time is 0.25~1 hour, preferably is 0.5 hour. In the reaction of (CH₂)$_{m-2}$CH=PPh₃ with

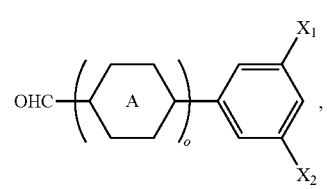

the reaction temperature is −10~5° C., preferably is −5° C.; the reaction time is 2~4 hours, preferably is 3 hours.

In the step 2 of synthetic method 5, the ratio between

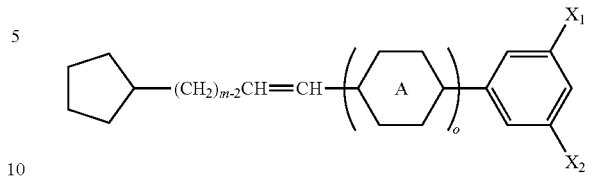

and Raney nickel catalyst is 100:5~35 by weight, preferably is 100:20; the reaction temperature is 0~100° C., preferably is 30° C., the reaction time is 1~10 hours, preferably is 6 hours.

In step 3 of synthetic method 5, the molar ratio of

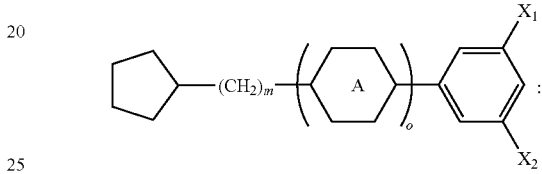

n-butyl lithium:difluorodibromomethane is 1:1~1.3:1~1.6, preferably is 1:1.1:1.2; the reaction temperature is −100 to −50° C., preferably is −60° C.; the reaction time is 0.5~4 hours, preferably is 2 hours.

In step 4 of synthetic method 5, said carbonate is selected from sodium carbonate or potassium carbonate; the molar ratio of

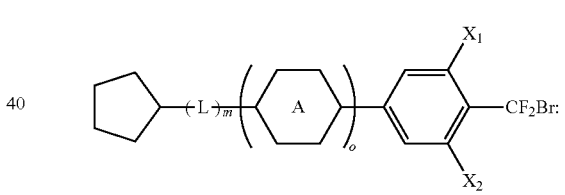

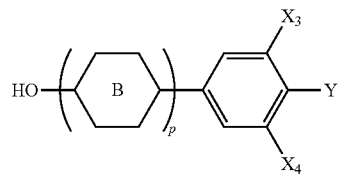

is 1:1~1.5, preferably is 1:1.2;

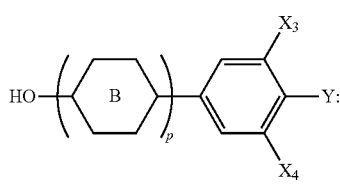

carbonate is 1:1~2; the reaction temperature is 30~100° C., preferably is 60° C.; the reaction time is 2~4 hours, preferably is 3 hours.

In step 1 of synthetic method 6, the molar ratio of

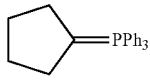

(cyclopentyllidenetriphenylphosphorane):

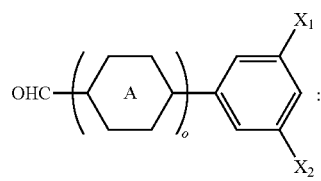

potassium t-butoxide is 1.1~1.3:1.1~1.3:1, preferably is 1~2:1~2:1; the reaction temperature is −10~5° C., preferably is −5° C., the reaction time is 2~4 hours, preferably is 3 hours.

In the step 2 of synthetic method 6, the ratio between

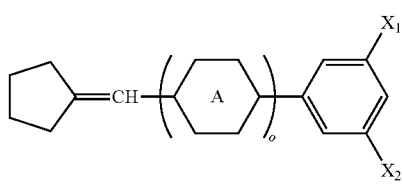

and Raney nickel catalyst is 100:5~35 by weight, preferably is 100:20; the reaction temperature is 0~100° C., preferably is 30° C.; the reaction time is 1~10 hours, preferably is 6 hours.

In step 3 of synthesis method 6, the molar ratio of

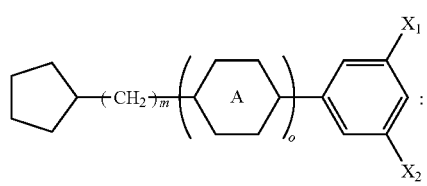

n-butyl lithium:difluorodibromomethane is 1:1~1.3:1~1.6, preferably is 1:1.1:1.2; the reaction temperature is −100 to −50° C., preferably is −60° C., the reaction time is 0.5~4 hours, preferably is 2 hour.

In step 4 of synthetic method 6, the molar ratio of

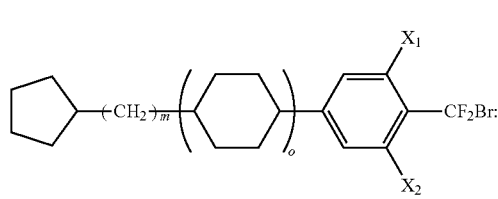

-continued

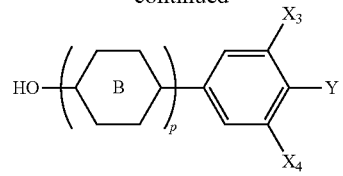

is 1:1~1.5, preferably is 1:1.2;

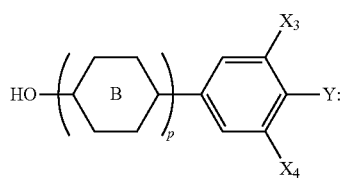

carbonate is 1:1~2; the reaction temperature is 30~100° C., preferably is 60° C.; the reaction time is 2~4 hours, preferably is 3 hours.

The reactions in all steps of the above methods were carried out in a solvent. Said solvent is selected from at least one of tetrahydrofuran, N,N-dimethylformamide, dimethylsulfoxide, ethanol and toluene.

The present invention provides the preparation and application of compounds of formula I in liquid crystal mixture or electro-optical display material. The liquid crystal mixture and electro-optical display material containing the compounds of formula I are also included in the scope of this patent.

BRIEF DESCRIPTION OF FIGURES

FIG. 1 are mass spectra. Where FIG. 1a is a mass spectrum of compound of formula 1-e, which are obtained in Example 1; FIG. 1b is a mass spectrum of compound of formula III 1.

EXAMPLES

The following examples illustrate the present invention without limiting it in any way. If no special instructions were given, the raw materials may be obtained from any commercial sources. GC is gas chromatography purity, MP is melting point, CP is clearing point, MS is mass spectrometry, $\Delta\in$ is dielectric anisotropy, $\Delta n$ is optical anisotropy. GC, MP, CP, MS, $\Delta\in$ and $\Delta n$ are measured by conventional methods.

Example 1

Preparation of the Compound of Formula 1-e (Method 2)

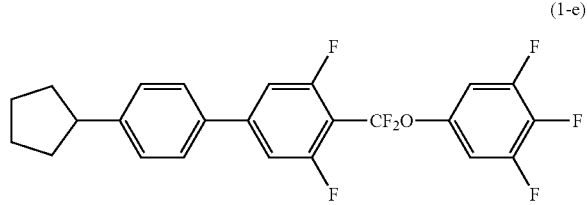

Step 1

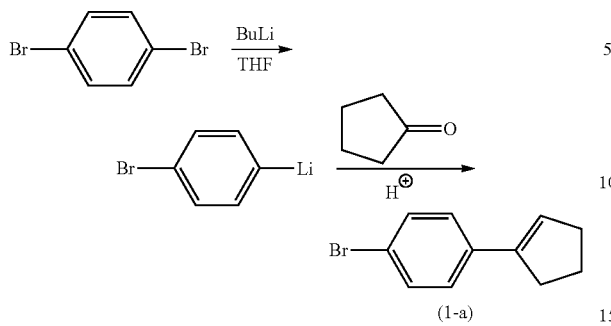

(1-a)

146 g (0.62 mol) of 1,4-dibromobenzene, 1 L of tetrahydrofuran were added into 2 L-three-flask, stirred to dissolve the solids under $N_2$, cooled to −80° C., then 2.5 M of n-butyllithium solution (250 mL, 0.62 mol) was added dropwise in 1 hour, and the solid was precipitated during the addition. After additional 0.5 h of stirring, 52 g (0.62 mol) of cyclopentanone in 50 mL of tetrahydrofuran was added dropwise at −80° C. in 0.5 h. After warming up to −50° C. (2 hours), the reaction mixture was then poured into a solution of concentrated hydrochloric acid (80 mL) and water (500 mL) with stirring. The aqueous phase was then separated and extracted with 200 mL of toluene, the combined organic phase was washed with water until neutral. The above organic solvent was evaporated under reduced pressure to afford alcohol intermediate, which was then dissolved in 400 mL of toluene, and 2 g of p-toluenesulfonic acid was added. The obtained mixture was refluxed for 4 hours until the dehydration reaction was completely, and the solvent was then evaporated. The residue was dissolved in petroleum ether and subjected to column chromatography packed with silica gel. 105 g of (1-a) was obtained, its GC purity is 96.8%, Yield: 76%.

Step 2

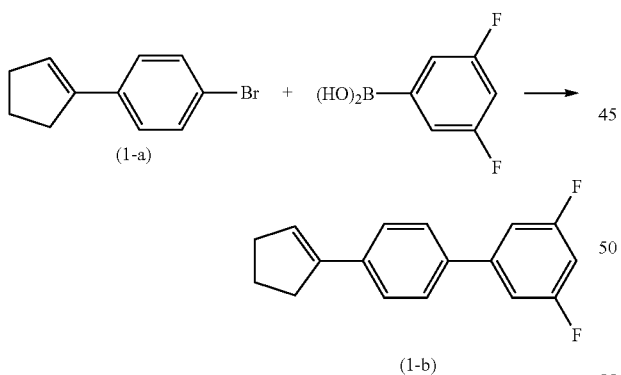

(1-b)

A mixture of 90 g (0.4 mol) of (1-a), 70 g (0.44 mol) of 3,5-difluorophenyl boronic acid, 300 mL of toluene, 300 mL of ethanol, 300 mL of water, 53 g (0.5 mol) of sodium carbonate and 3.0 g of tetrakis(triphenylphosphine) palladium in a 2 L-three-necked flask was refluxed under $N_2$ for 5 hours. After cooled to room temperature, the organic phase was separated, and the aqueous phase was extracted with 100 mL of toluene. The combined organic phase was washed with water to neutral, and the solvent was distilled off under reduced pressure. The obtained residue was then dissolved in 300 mL of petroleum ether and purified by silica gel column chromatography. 95 g of (1-b) was obtained as pale yellow crystals by the recrystallization from 300 mL of ethanol; GC purity: 98.3%, Yield: 93%.

Step 3

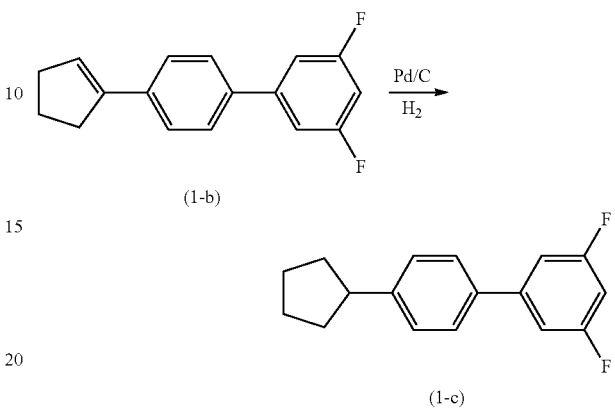

(1-c)

95 g of 1-b in 200 mL of toluene, 100 mL of ethanol, and 19 g of Raney nickel catalyst in 2 L-flask was hydrogenated at atmospheric pressure of hydrogen for 6 hours until the theoretical amount of hydrogen was consumed. Raney nickel catalyst was then removed by filtration, and the solvent was evaporated to give 10 g of 1-c as white solid. GC purity: 98.0%; Yield: 96.8%.

Step 4

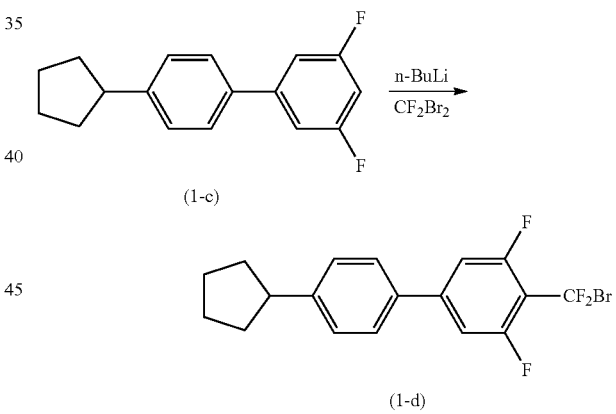

(1-d)

To a solution of 65 g (0.25 mol) of 1-c in 330 mL of tetrahydrofuran in a 1 L-three-necked flask, 110 mL (0.275 mol) of n-BuLi was added dropwise at −60° C. under a nitrogen atmosphere in 1 hour, and then 63 g (0.3 mol) of difluorodibromomethane in 20 mL of tetrahydrofuran was added dropwise for a further 0.5 h at the same temperature. The mixture was then warmed to −40° C. (2 hours), and was poured into 27 mL of concentrated hydrochloric acid and 500 mL of water with stirring. The aqueous phase was extracted once with 200 mL of petroleum ether, and the combined organic phase was washed with brine to neutral. The solvent was then evaporated under reduced pressure to give a yellow liquid. The yellow liquid was dissolved in petroleum ether again and subjected to column chromatography packed with silica gel. 93 g of 1-d as pale yellow liquid was obtained. GC purity: 72.3%

Step 5

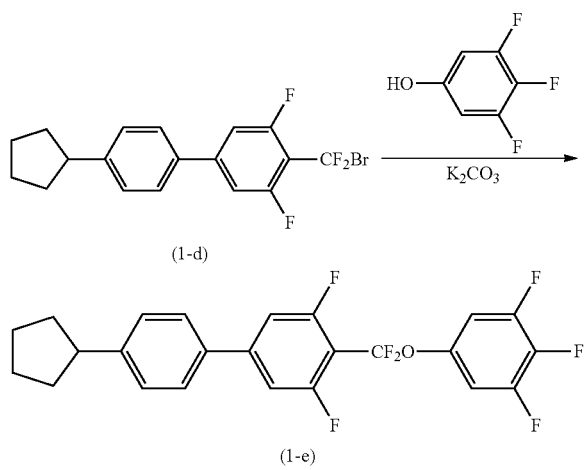

A mixture of 65 g (0.121 mol) of 1-d, 20.7 g (0.14 mol) of 3,4,5-trifluorophenol, and 35.9 g (0.26 mol) of potassium carbonate in 500 mL of dimethyl sulfone in a 1 L-three-necked flask was heated with stirring at 60° C. in a water bath for 3 hours. The resulting reaction mixture was poured into 1 L of water, and was extracted with petroleum ether (150 mL×2). The organic phase was washed with water, and removed by distillation under reduced pressure. The crude product was subjected to column chromatography packed with silica gel, 30 g of 1-e as white crystals was obtained by recrystallization from 150 mL of petroleum ether (4 times). The characterization data of 1-e are as follow:

GC purity: 99.92%
MP: 49° C.
CP: 22° C.
MS: m/z (%) 454 (M$^+$, 1.9), 307 (100), 265 (14.1), 252 (7.0), 239 (3.9)
Δn [589 nm, 20° C.]: 0.142
Δ∈ [1 KHz, 20° C.]: 20.1

The mass spectrum of the compound 1-e was shown in FIG. 1a. On the basis of the above MS data, the structure of 1-e was confirmed.

The properties of the compound 1-e obtained in Example 1 was determined according to the following steps:

10 parts of compound 1-e (by weight) was dissolved in 90 parts of mother liquid crystal composition which exhibits a clearing point (cp) of 80° C. to obtain a mixture. The mixture exhibits a clearing point (cp) of 82.4° C.

10 parts of

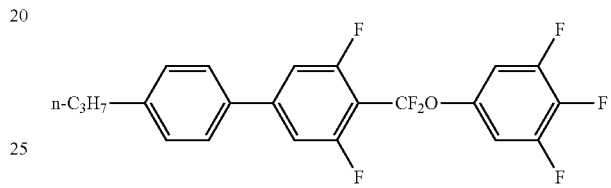

[4-(difluoro(3,4,5-trifluorophenoxy)methyl)-3,5-difluoro-4'-n-propyl-1,1'-biphenyl) (by weight) was dissolved in 90 parts of mother liquid crystal composition to obtain a mixture. The mixture exhibits a clearing point (cp) of 78.8° C.

The mother liquid crystal composition consisting of compounds below.

| compound | ratio |
|---|---|
| n-C$_3$H$_7$—[cyclohexyl]—[cyclohexyl]—CH=CH$_2$ | 48 |
| n-C$_3$H$_7$—[cyclohexyl]—[cyclohexyl]—CH=CH—CH$_3$ | 10 |
| C$_2$H$_5$—[phenyl]—[difluorophenyl]—[phenyl]—F | 8 |
| H$_3$C—[phenyl]—[cyclohexyl]—[cyclohexyl]—CH$_2$CH$_2$CH=CH$_2$ | 8 |
| C$_2$H$_5$—[phenyl]—[fluorophenyl]—[phenyl]—n-C$_3$H$_7$ | 8 |
| n-C$_3$H$_7$—[cyclohexyl]—[phenyl]—[phenyl]—[cyclohexyl]—n-C$_3$H$_7$ | 8 |

According to the above obtained data, compared with the similar compound, the use of compound I-e can increase the clearing point CP. The clearing point of the material is as high as possible used in the liquid crystal display device. This indicates that the present invention provides a compound of formula I which has the important application value in the field of electro-optical display material.

The compounds shown below can be synthesized by a method similar to that described in example 1 using the corresponding reactants. The physical properties of the prepared compounds are listed below.

(113)

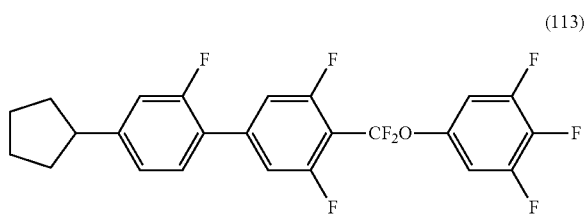

GC purity: 99.95%
MP: 43° C.
CP: 21° C.
Δn [589 nm, 20° C.]: 0.14
Δ∈ [1 KHz, 20° C.]: 24

(1111)

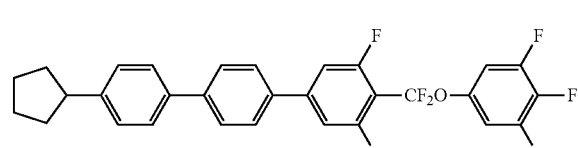

GC purity: 99.95%
MP: 117.5° C.
CP: 52° C.
MS: m/z (%) 566 (M+, 0.9), 307 (100), 265 (6.2), 252 (3.4), 239 (1.8)
Δn [589 nm, 20° C.]: 0.155
Δ∈ [1 KHz, 20° C.]: 26.5

The mass spectrum of the compound III1 is shown in FIG. 1b.

The compounds of formula I shown below can be synthesized by a method similar to that described above using the corresponding reactants.

The physical properties of

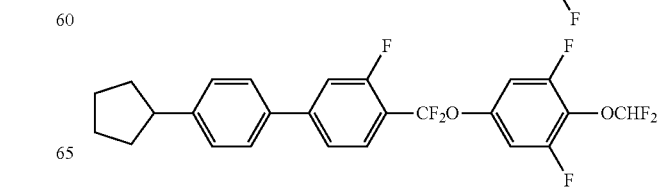

are as follows:
GC purity: 99.90%
MP: 91° C.
CP: 147° C.
Δn [589 nm, 20° C.]: 0.16
Δ∈ [1 KHz, 20° C.]: 21

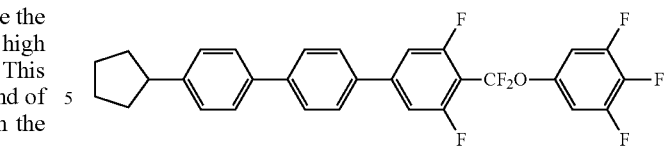

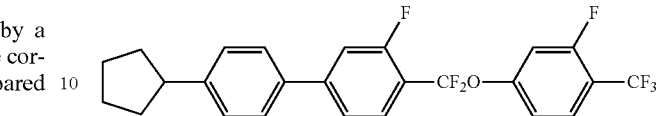

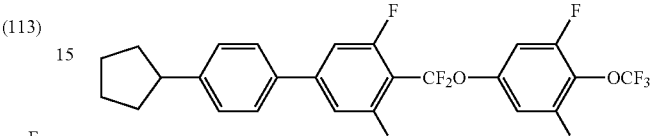

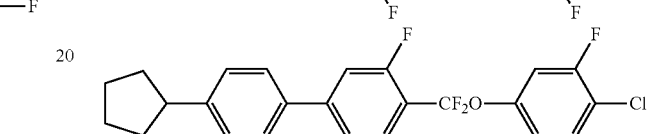

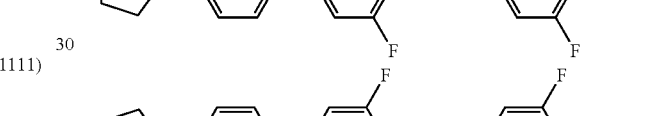

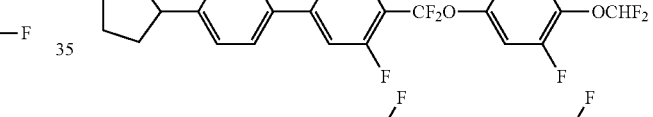

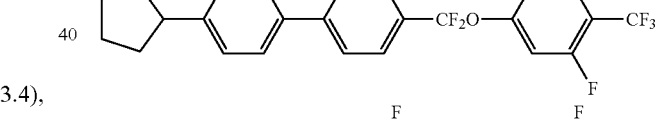

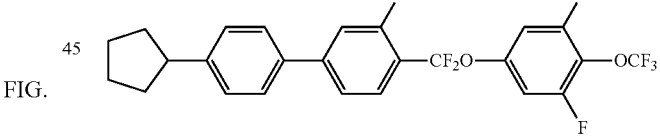

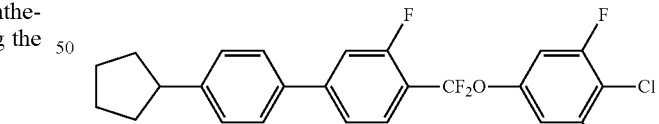

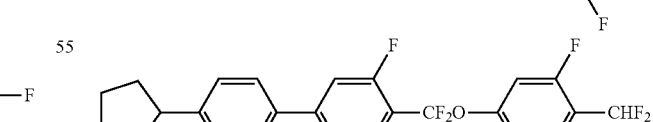

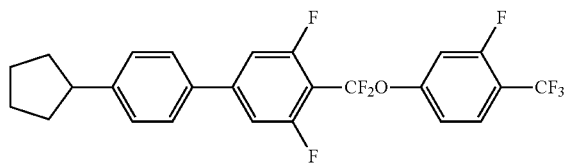

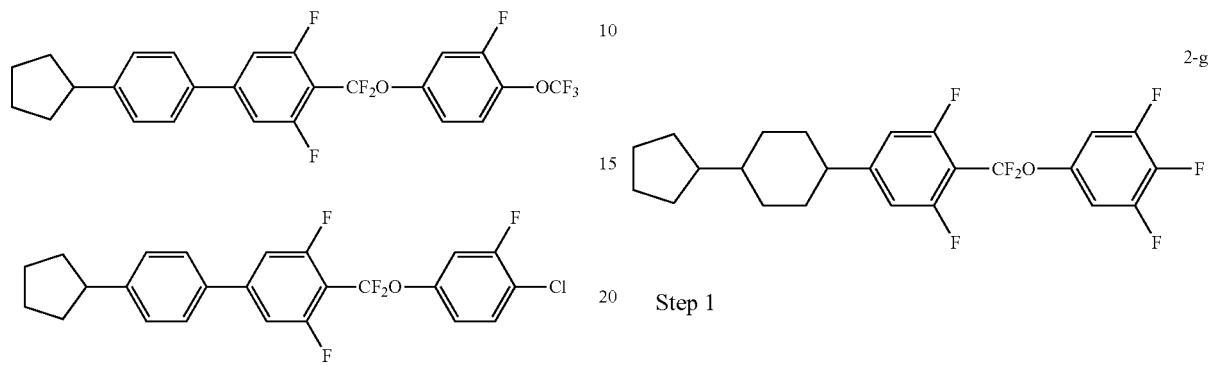

The properties of these compounds show it is the desired compounds.

Example 2

Preparation of the Compound of Formula 2-g
(Formula II1) (Method 1)

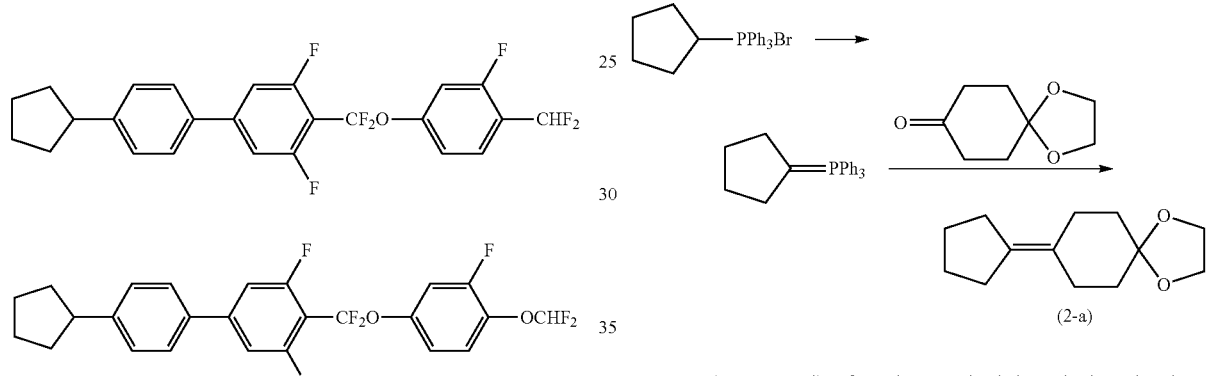

Step 1

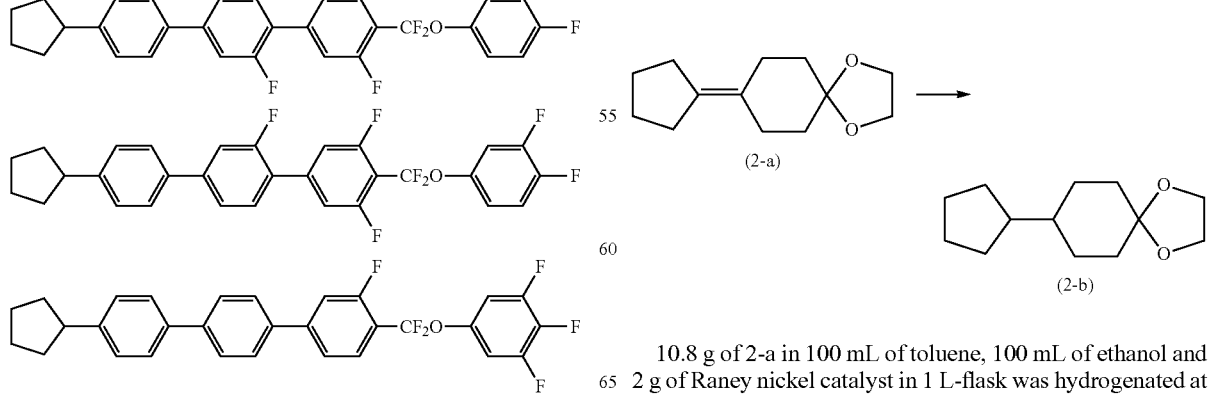

69 g (0.168 mol) of cyclopentyl triphenyl phosphonium bromide, and 600 mL of tetrahydrofuran were added into a 1 L-three-necked flask, the reaction mixture was stirred at −10° C. and 18.8 g (0.168 mol) of potassium t-butoxide was added portionwise to give an orange mixture and stirred for additional 1 hour. A solution of 22 g (0.14 mol) of 1,4-cyclohexanedione monoethylene acetal in 150 mL of methyl t-butyl ether was added dropwise at 0° C., and the obtained mixture was then stirred for 3 hours. The above mixture was poured into 500 mL of water, and the water layer was extracted with dichloromethane. The organic phase was concentrated, and the residue was dissolved in petroleum ether again, and subjected to silica gel column separation to give 10.8 g of 2-a.

Step 2

10.8 g of 2-a in 100 mL of toluene, 100 mL of ethanol and 2 g of Raney nickel catalyst in 1 L-flask was hydrogenated at atmospheric pressure of hydrogen for 6 hours until the theoretical amount of hydrogen was absorbed. Raney nickel catalyst was removed by filtration, and the solvent was evaporated under reduced pressure to give 10 g of 2-b.

Step 3

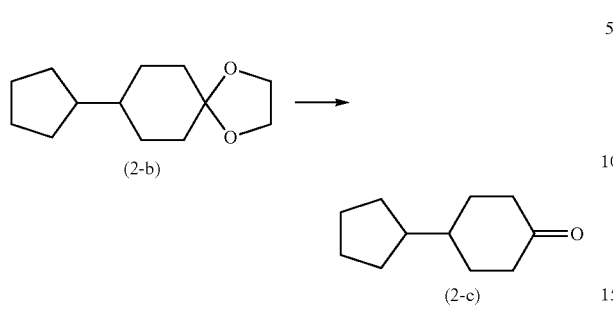

A solution of 10 g of 2-b obtained in step 2, 50 mL of toluene and 20 mL of 85% formic acid in 250 mL of flask was stirred for 20 hours at room temperature. The organic phase was washed with water and dried over anhydrous sodium sulfate. After removal of solvent, 6.5 g of 2-c was obtained.

Step 4

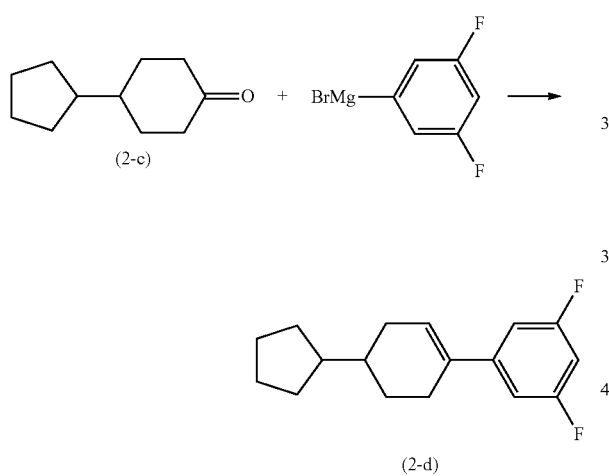

1 g (0.042 mol) of magnesium turnings and 30 mL of anhydrous tetrahydrofuran was added into a 250-mL of three-necked flask, 7.7 g (0.04 mol) of 3,5-difluoro-bromobenzene in 30 mL of anhydrous tetrahydrofuran was added dropwise, and then heated to reflux for 0.5 hour. To the above solution 6.5 g (0.04 mol) (2-c) in 20 mL of tetrahydrofuran was added dropwise at room temperature, and then refluxed for 1.5 hours. The reaction mixture was then poured into dilute aqueous hydrochloric acid, the aqueous phase was separated and extracted with toluene, the combined organic phase was washed with water until neutral, the solvent was then evaporated under reduced pressure to give the alcohol intermediate. A solution of the above intermediate and 0.5 g of p-toluenesulfonic acid in 50 mL of toluene was refluxed until the dehydration reaction was complete, and then the solvent was evaporated. The residue was dissolved in petroleum ether and subjected to column chromatography packed with silica gel to give 5.2 g of 2-d. GC purity: 98.2%.

Step 5

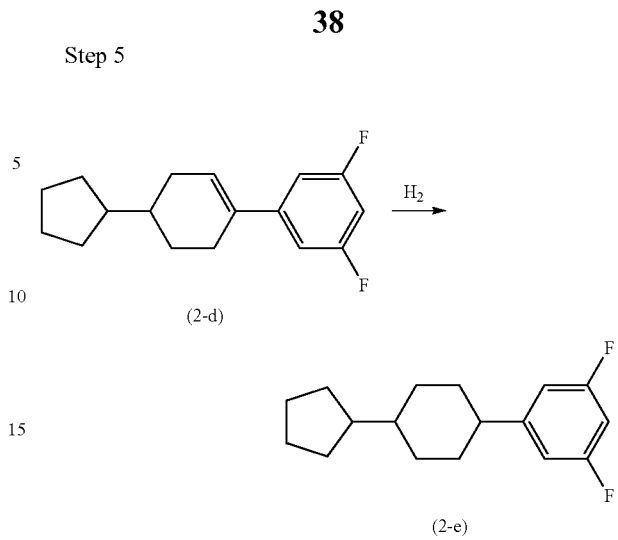

5.2 g of 2-d in 30 mL of toluene, 40 mL of ethanol and 1 g of Raney nickel catalyst in 1 L-flask was hydrogenated at atmospheric pressure of hydrogen for 6 hours until the theoretical amount of hydrogen was absorbed, After Raney nickel catalyst was removed by filtration, the solvent was evaporated under reduced pressure to give 5 g of 2-e, GC purity: 98.2%.

Step 6

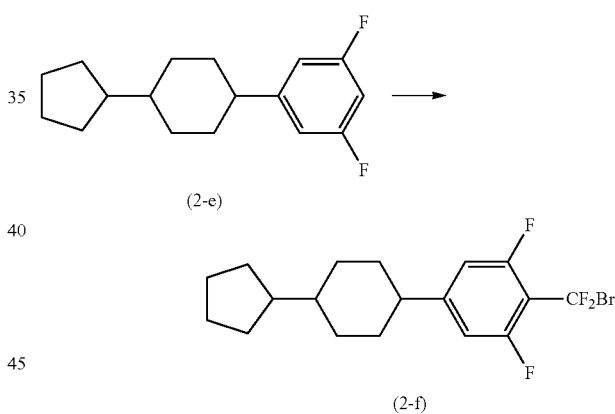

8.4 mL (0.021 mol) of n-BuLi was added dropwise at −60° C. under a nitrogen atmosphere to a solution of 5 g (0.019 mol) of 2-e in 30 mL of tetrahydrofuran in a 250 mL of three-necked flask in 1 h with stirring. Then 4.79 g (0.0228 mol) of difluorodibromomethane in 20 mL of tetrahydrofuran was added dropwise in 0.5 h at the same temperature. The mixture was then warmed to −40° C. (2 hours), and poured into 3 mL of concentrated hydrochloric acid in 50 mL of water, the aqueous phase was extracted once with 20 mL of petroleum ether. The combined organic layer was washed with brine to neutral, and the solvent was evaporated under reduced pressure to give a yellow liquid. The yellow liquid was dissolved in petroleum ether and subjected to column chromatography packed with silica gel to give 5.9 g of 2-f as pale yellow liquid. GC purity: 52.9%.

Step 7

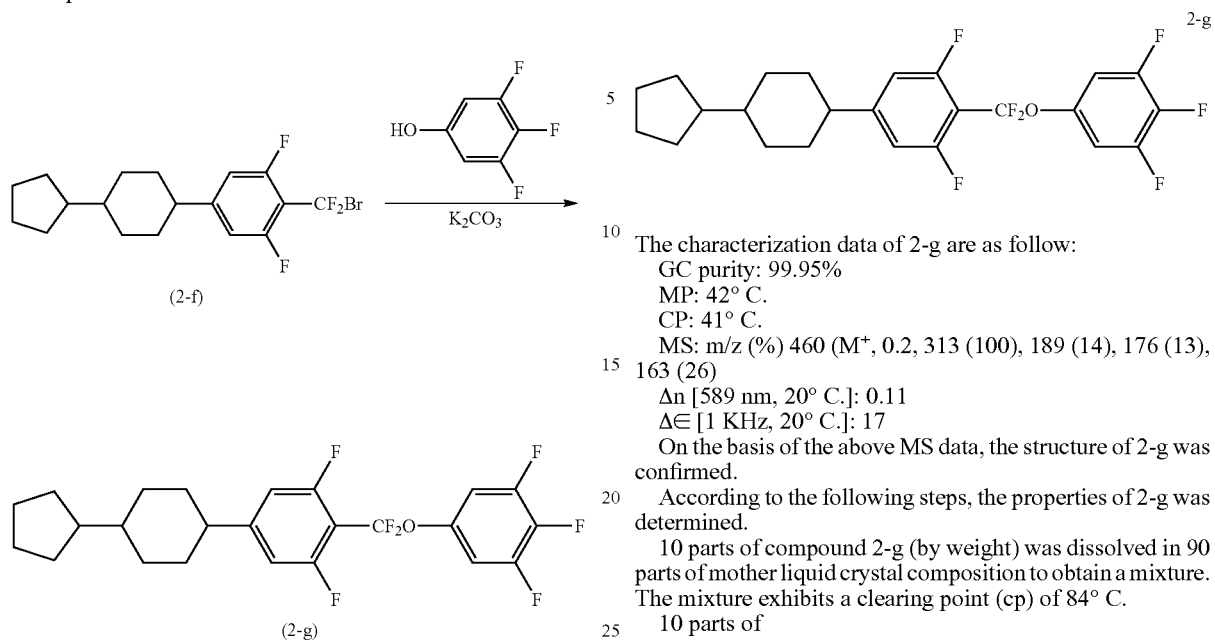

(2-f)

(2-g)

A mixture of 5.9 g (0.008 mol) of 2-f, 1.4 g (0.0095 mol) of 3,4,5-trifluorophenol, 2.6 g (0.019 mol) of potassium carbonate, and 50 mL of dimethyl sulfone was heated at 60° C. in a 250 mL of three-necked flask in a water bath with stirring for 3 hours. The resulting brown reaction mixture was then poured into 100 mL of water, and extracted with petroleum ether (20 mL×3), washed with water. After removal of the solvent, the residue was subjected to column chromatography packed with silica gel and recrystallized from 15 mL of petroleum ether (4 times) to obtain 1.0 g of 2-g as white.

The characterization data of 2-g are as follow:
GC purity: 99.95%
MP: 42° C.
CP: 41° C.
MS: m/z (%) 460 ($M^+$, 0.2, 313 (100), 189 (14), 176 (13), 163 (26)
Δn [589 nm, 20° C.]: 0.11
Δ∈ [1 KHz, 20° C.]: 17
On the basis of the above MS data, the structure of 2-g was confirmed.
According to the following steps, the properties of 2-g was determined.
10 parts of compound 2-g (by weight) was dissolved in 90 parts of mother liquid crystal composition to obtain a mixture. The mixture exhibits a clearing point (cp) of 84° C.
10 parts of

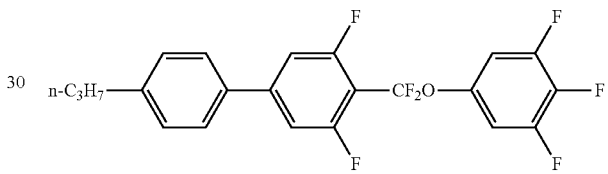

(by weight) was dissolved in 90 parts of mother liquid crystal composition to obtain a mixture. The mixture exhibits a clearing point (cp) of 78.8° C.
In the above test the mother liquid crystal composition (Mo) consisting of compounds below:

| compound | ratio |
|---|---|
| 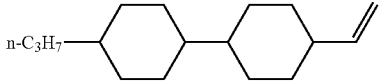 | 48 |
| 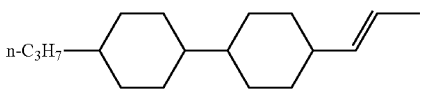 | 10 |
| 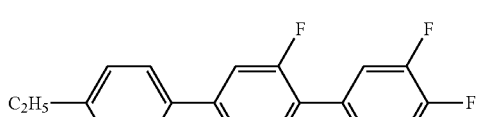 | 8 |
| 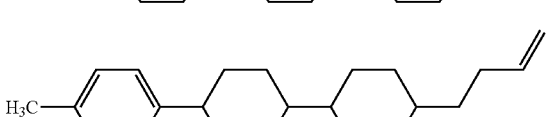 | 8 |
| 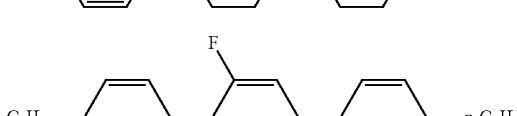 | 8 |

| compound | ratio |
|---|---|
| 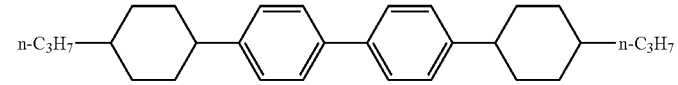 | 8 |

According to the above obtained data, compared with the similar compound, the use of compound I-e can increase the clearing point CP. The clearing point of the material is as high as possible used in the liquid crystal display device. This indicates that the present invention provides a compound of formula I which has the important application value in the field of electro-optical display material.

The compounds of formula I shown below can be synthesized by a method similar to that described in method 1 using the corresponding reactants.

the physical properties of

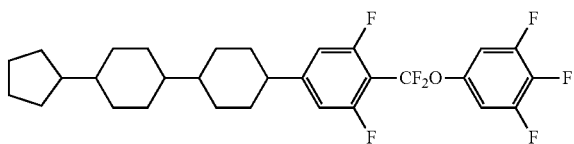

are as follows:
GC purity: 99.95%
MP: 105° C.
CP: 158° C.
Δn [589 nm, 20° C.]: 0.12
Δε [1 KHz, 20° C.]: 17

The properties of this compound show it is the desired compound.

Example 3

Preparation of the Compound of Formula 3-d (Method 3)

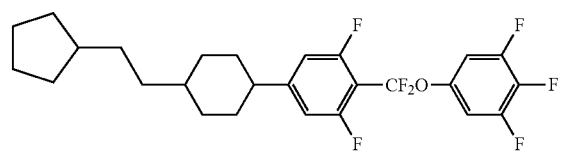

Step 1

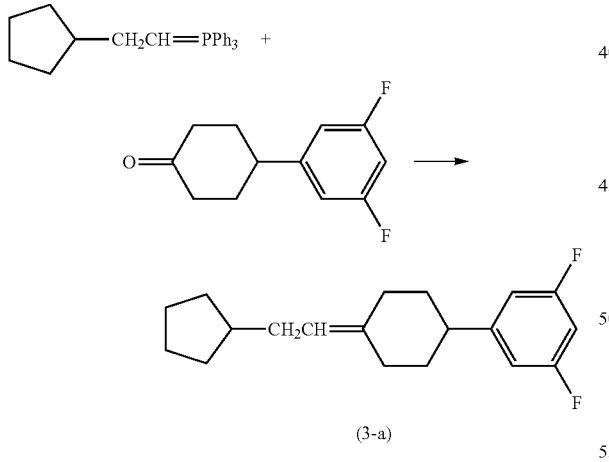

48.3 g (0.11 mol) of 2-cyclopentyl-1-bromoethyl triphenyl phosphonium and 200 mL of tetrahydrofuran were added into a 500-mL of three-necked flask, at −5° C., 12.5 g (0.11 mol) of potassium t-butoxide was added portionwise, and the obtained mixture was stirred at the same temperature for 0.5 h. A solution of 21 g (0.1 mol) of 4-(3,5-difluorophenyl) cyclohexanone in 60 mL of tetrahydrofuran was then added dropwise at 0° C. and was stirred for 3 hours at room temperature.

The above mixture was poured into 400 mL of water with stirring, and the water layer was extracted with ethyl acetate. The combined organic layer was washed with water until neutral, and dried over anhydrous sodium sulfate. After removal of solvent, the residue was dissolved in petroleum ether again, and subjected to silica gel column separation to give 23.2 g of 3-a. GC purity: 98.3%.

Step 2

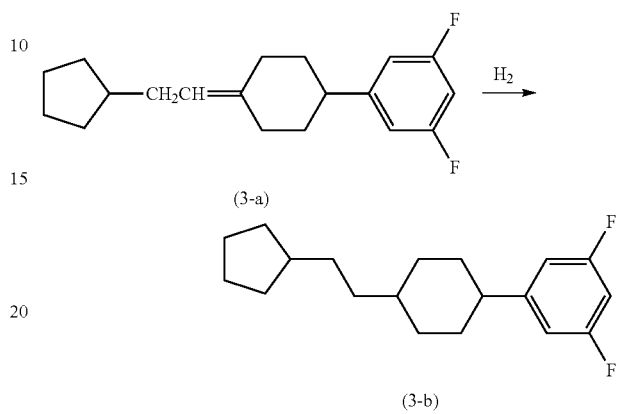

23.2 g of 3-a in 100 mL of toluene, 100 mL of ethanol and 5 g of Raney nickel catalyst in 1 L-flask was hydrogenated at atmospheric pressure of hydrogen for 6 hours until the theoretical amount of hydrogen was absorbed. Raney nickel catalyst was removed by filtration, and the solvent was evaporated under reduced pressure to give 22 g of 3-b. GC purity: 98.0%, yield: 94.8%.

Step 3

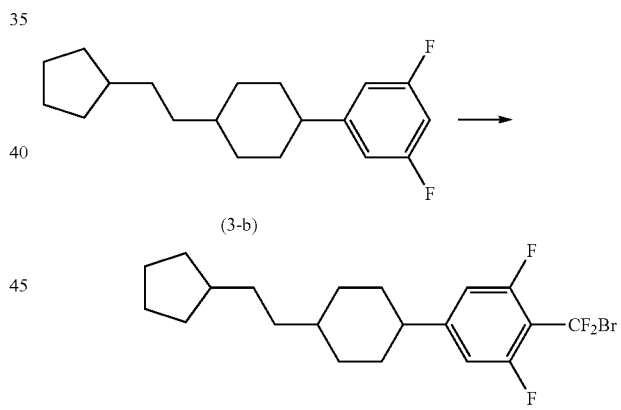

33 mL (0.083 mol) of n-BuLi was added dropwise at −60° C. under a nitrogen atmosphere to a solution of 22 g (0.075 mol) of 3-b in 100 mL of tetrahydrofuran in a 250 mL of three-necked flask in 1 h. Then 18.9 g (0.09 mol) of difluorodibromomethane in 20 mL of tetrahydrofuran was added dropwise in 0.5 h at the same temperature. The mixture was then warmed to −40° C. (2 hours), and poured into 7 mL of concentrated hydrochloric acid in 200 mL of water, the aqueous phase was extracted once with 100 mL of petroleum ether. The combined organic layer was washed with brine to neutral, and the solvent was evaporated under reduced pressure to give a yellow liquid. The yellow liquid was dissolved in petroleum ether and subjected to column chromatography packed with silica gel to give 26.8 g of 3-c as pale yellow liquid. GC purity: 55.6%.

Step 4

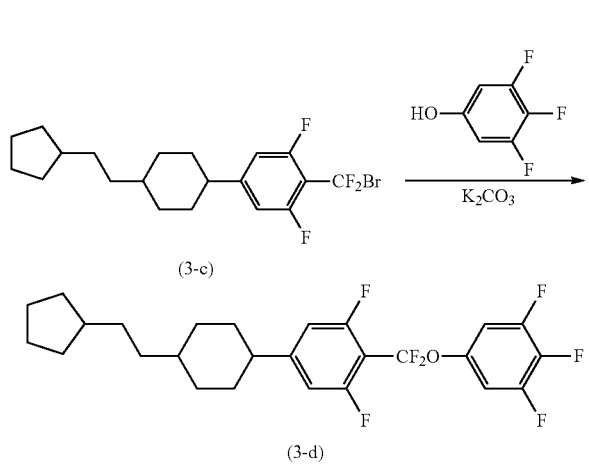

A mixture of 26.8 g (0.035 mol) of 3-c, 6.2 g (0.042 mol) of 3,4,5-trifluorophenol, 11.3 g (0.082 mol) of potassium carbonate, and 150 mL of dimethyl sulfone was heated at 60° C. in a 250 mL of three-necked flask in a water bath with stirring for 3 hours. The resulting brown reaction mixture was then poured into 300 mL of water, and extracted with petroleum ether (90 mL×2), washed with water. After removal of the solvent, the residue was subjected to column chromatography packed with silica gel. 4.9 g of 3-d as white crystals was obtained by recrystallization from 100 mL of petroleum ether (5 times). The characterization data of 3-d are as follow:

GC purity: 99.95%
Mp: 41° C.
Cp: 38° C.
MS: m/z (%) 488 (M$^+$, 0.2), 341 (100)
Δn [589 nm, 20° C.]: 0.1
Δ∈ [1 KHz, 20° C.]: 17

On the basis of the above MS data, the structure of 3-d was confirmed.

The compounds of formula I shown below can be synthesized by a method similar to that described in method 3 using the corresponding reactants.

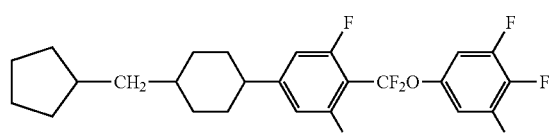

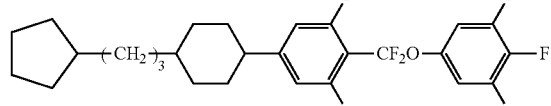

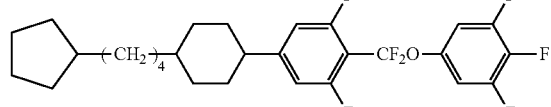

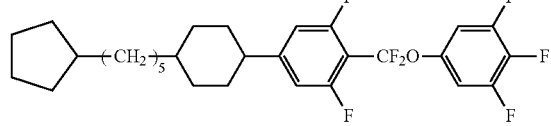

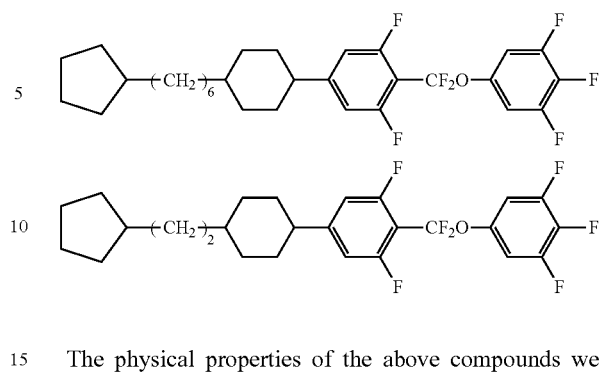

The physical properties of the above compounds were measured.

Example 4

Preparation of the Compound of Formula 4-c (Method 4)

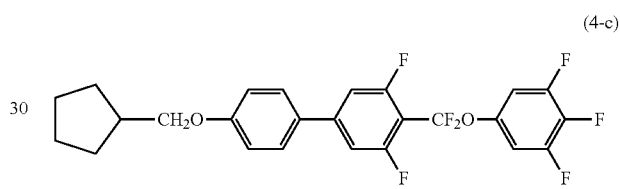

Step 1

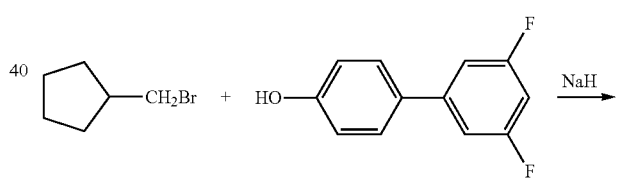

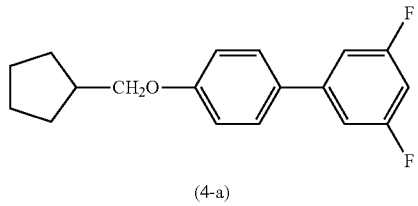

To a solution of 20.6 g (0.1 mol) of 4-(3,5-difluorophenyl)phenol in 200 mL of N,N-dimethylformamide in a 500 mL of three-necked flask, 4.8 g (0.12 mol) of 60% sodium hydride was added portionwise under nitrogen with stirring at 30° C., and then 16.3 g (0.1 mol) of cyclopentyl methyl bromide was added dropwise. After the reaction was stuffed for 20 hours, it was poured into 500 mL of water, and was extracted with hot petroleum ether (200 mL×2). The combined organic phases was washed with water to neutral, and the solvent was then distilled off under reduced pressure. 15 g of 4-a as white crystals was obtained by recrystallization from ethanol. GC purity: 98.9%.

Step 2

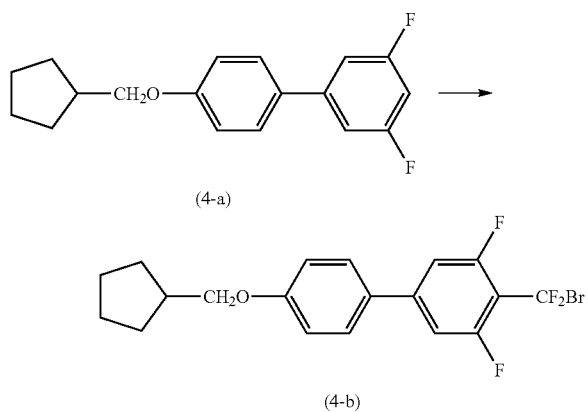

23 mL (0.057 mol) of n-BuLi was added dropwise at −60° C. under a nitrogen atmosphere to a solution of 15 g (0.052 mol) of 4-a in 100 mL of tetrahydrofuran in a 250 mL of three-necked flask in 1 h. Then 13.2 g (0.062 mol) of difluorodibromomethane in 20 mL of tetrahydrofuran was added dropwise in 0.5 h at the same temperature. The mixture was then warmed to −40° C. (2 hours), and poured into 6 mL of concentrated hydrochloric acid in 200 mL of water, the aqueous phase was extracted once with 100 mL of petroleum ether. The combined organic layer was washed with brine to neutral, and the solvent was evaporated under reduced pressure to give a yellow liquid. The yellow liquid was dissolved in petroleum ether and subjected to column chromatography packed with silica gel to give 18.4 g of 4-b as pale yellow liquid. GC purity: 74.6%.

Step 3

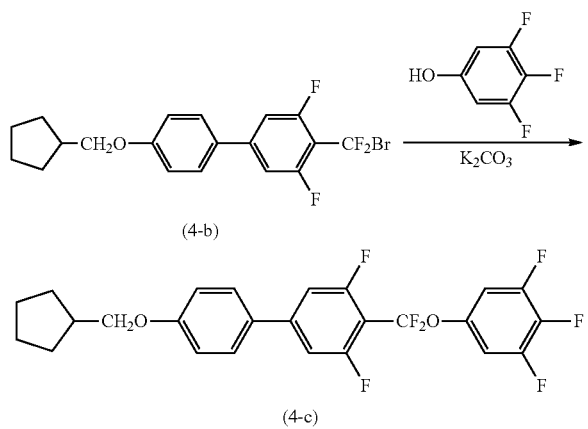

A mixture of 18.4 g (0.033 mol) of 4-b, 5.9 g (0.04 mol) of 3,4,5-trifluorophenol, 11.0 g (0.08 mol) of potassium carbonate, and 120 mL of dimethyl sulfone was heated at 60° C. in a 250 mL of three-necked flask in a water bath with stirring for 3 hours. The resulting brown reaction mixture was then poured into 300 mL of water, and extracted with petroleum ether (90 mL×2), washed with water. After removal of the solvent, the residue was subjected to column chromatography packed with silica gel. 6.4 g of 4-c as white crystals was obtained by recrystallization from 100 mL of petroleum ether (5 times).

The characterization data of 4-c are as follow:

GC purity: 99.92%

Mp: 73° C.

Cp: 4° C.

MS: m/z (%) 484 (M⁺, 0.05), 255 (100), 337 (10)

Δn [589 nm, 20° C.]: 0.15

Δ∈ [1 KHz, 20° C.]: 16

On the basis of the above MS data, the structure of 4-c was confirmed.

The compounds of formula I shown below can be synthesized by a method similar to that described in method 4 using the corresponding reactants.

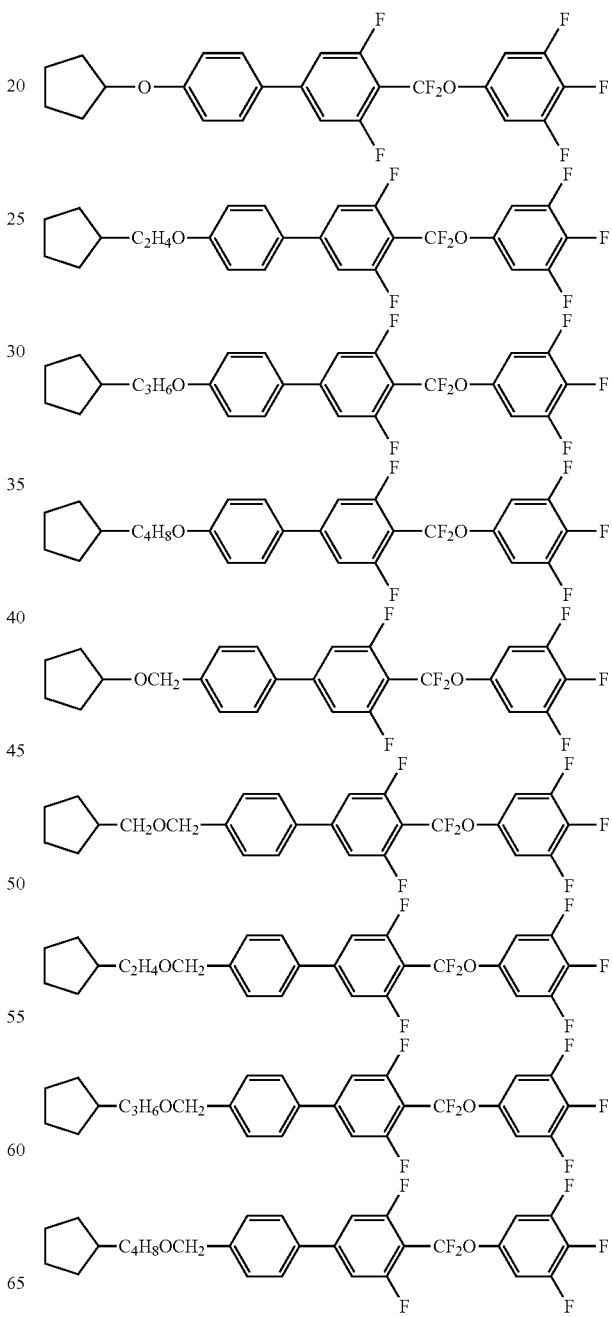

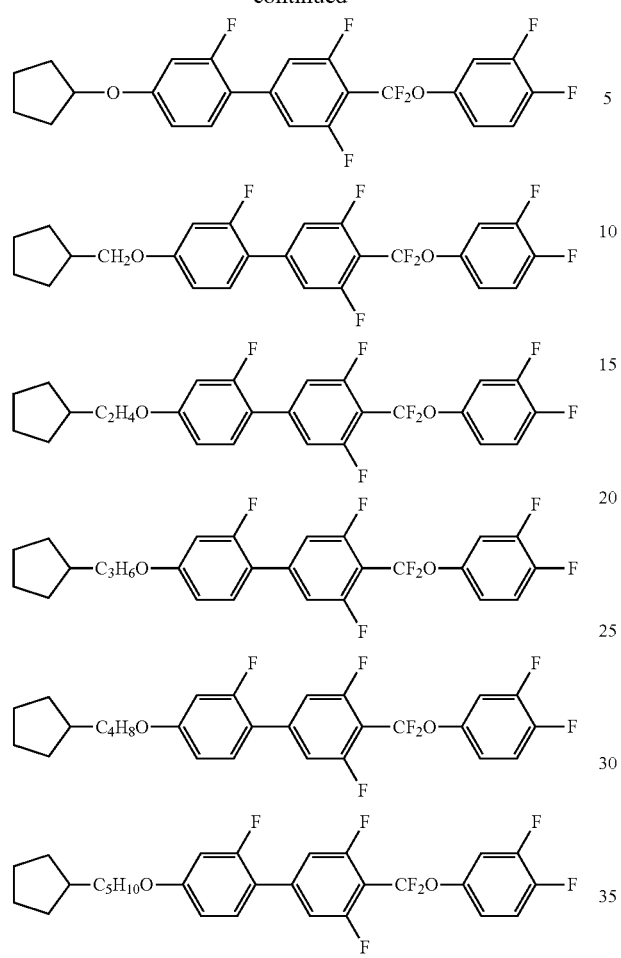

The physical properties of the above compounds of formula I were measured.

Example 5

Preparation of the Compound of Formula 5-d (Method 5 and Method 6)

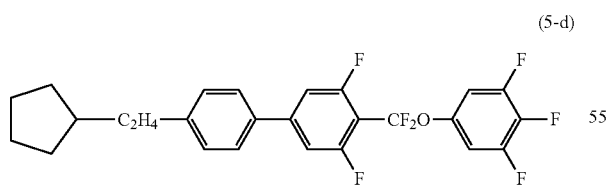
(5-d)

Step 1

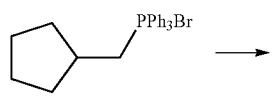

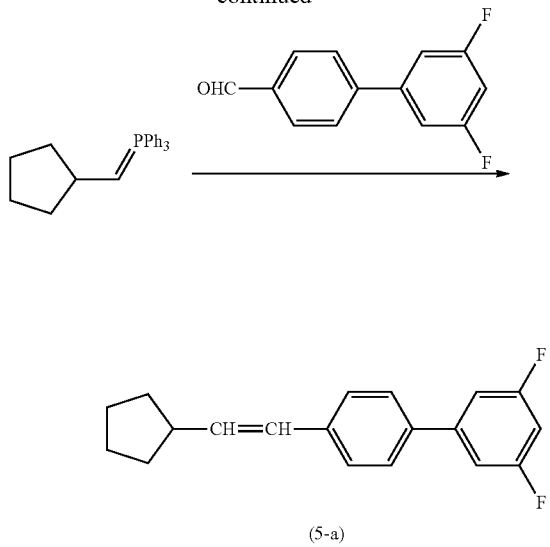

(5-a)

0.12 mol of cyclopentyl bromomethyl triphenyl phosphonium and 200 mL of tetrahydrofuran were added into a 500-mL of three-necked flask, at −5° C., 0.12 mol of potassium t-butoxide was added portionwise, and the obtained mixture was stirred at the same temperature for 0.5 h. A solution of 0.1 mol of 4-(3,5-difluorophenyl)benzaldehyde in 80 mL of tetrahydrofuran was then added dropwise at 0° C. and was stirred for 3 hours at room temperature.

The above mixture was poured into 400 mL of water with stirring, and the water layer was extracted with dichloromethane. The combined organic layer was washed with water until neutral, and dried over anhydrous sodium sulfate. After removal of solvent, the residue was dissolved in petroleum ether again, and subjected to silica gel column separation to give 20.0 g (0.08 mol) of 5-a. GC purity: 98.0%.

Step 2

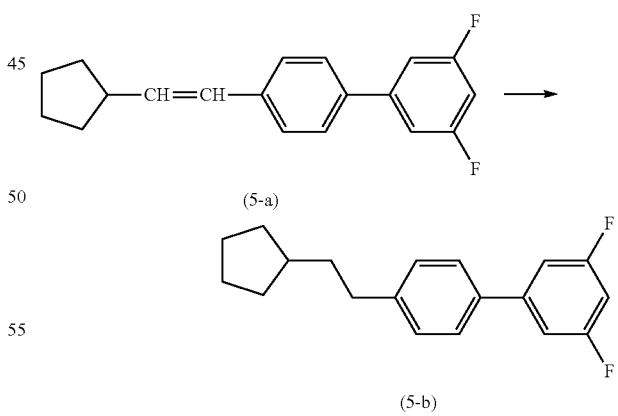

20 g of 5-a in 100 mL of toluene, 100 mL of ethanol and 5 g of Raney nickel catalyst in 1 L-flask was hydrogenated at atmospheric pressure of hydrogen for 6 hours until the theoretical amount of hydrogen was absorbed. After removal of Raney nickel catalyst by filtration, the solvent was evaporated under reduced pressure to give 19.5 g of 5-b. GC purity: 98.0%, yield: 97.5%.

Step 3

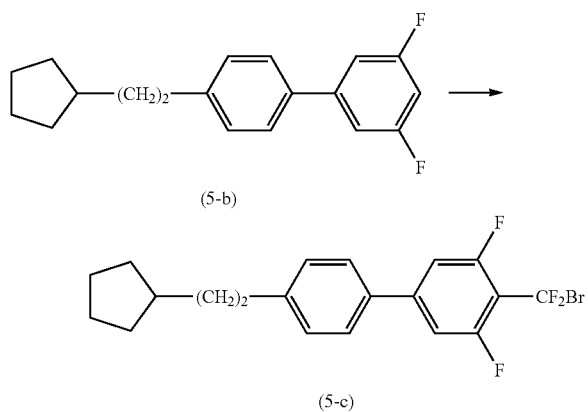

30 mL (0.075 mol) of n-BuLi was added dropwise at −60° C. under a nitrogen atmosphere to a solution of 19.5 g (0.068 mol) of 5-b in 100 mL of tetrahydrofuran in a 250 mL of three-necked flask in 1 h. Then 17.2 g (0.082 mol) of difluorodibromomethane in 20 mL of tetrahydrofuran was added dropwise in 0.5 h at the same temperature. The mixture was then warmed to −40° C. (2 hours), and poured into 7 mL of concentrated hydrochloric acid in 200 mL of water, the aqueous phase was extracted once with 100 mL of petroleum ether. The combined organic layer was washed with brine to neutral, and the solvent was evaporated under reduced pressure to give a yellow liquid. The yellow liquid was dissolved in petroleum ether and subjected to column chromatography packed with silica gel to give 24 g of 5-c as pale yellow liquid. GC purity: 73.7%.

Step 4

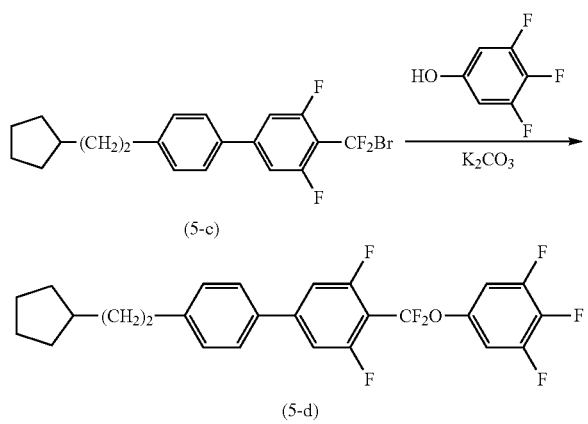

A mixture of 24 g (0.042 mol) of 5-c, 7.5 g (0.051 mol) of 3,4,5-trifluorophenol, 13.8 g (0.1 mol) of potassium carbonate, and 120 mL of dimethyl sulfone was heated at 60° C. in a 250 mL of three-necked flask in a water bath with stirring for 3 hours. The resulting brown reaction mixture was then poured into 300 mL of water, and extracted with petroleum ether (90 mL×2), washed with water. After removal of the solvent, the residue was subjected to column chromatography packed with silica gel. 5.9 g of 5-d as white crystals was obtained by recrystallization from 100 mL of petroleum ether (5 times).

The characterization data of 5-d are as follow:
GC purity: 99.92%
Mp: 55° C.
Cp: 5° C.
MS: m/z (%) 482 (M$^+$, 0.05), 253 (100), 252 (70), 335 (20)
Δn [589 nm, 20° C.]: 0.13
Δ∈ [1 KHz, 20° C.]: 17
On the basis of the above MS data, the structure of 5-d was confirmed.

The compounds of formula I shown below can be synthesized by a method similar to that described in method 5 using the corresponding reactants.

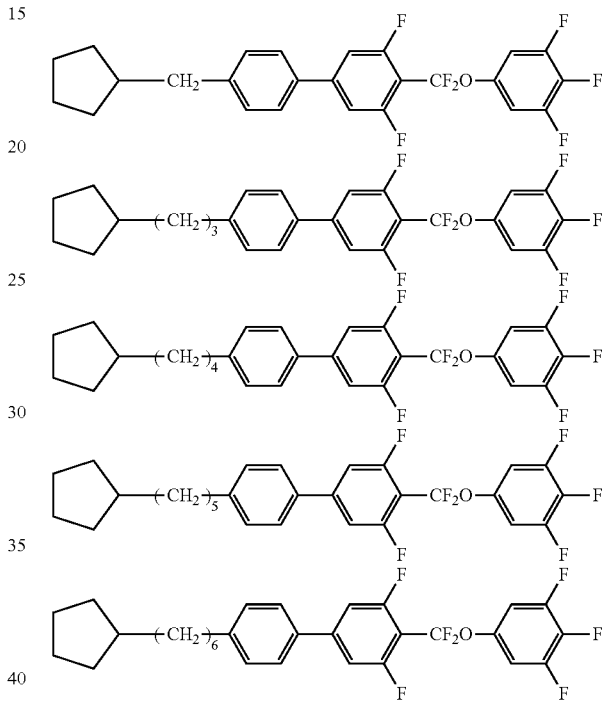

INDUSTRIAL APPLICATIONS

The liquid crystal compounds are generally formulated into a mixture. The mixtures having a high clearing point and low rotational viscosity are required. Clearing point of the mixture and the rotational viscosity depends on the composition of a mixture, as well as the clearing point and rotational viscosity of single crystal. Although liquid crystal compound containing a difluoromethyleneoxy group (—CF$_2$O—) has a low rotational viscosity, its clearing point compared with those compounds which contain other linking group such as —CH$_2$O—, —C≡C—, —COO—, —CH$_2$CH$_2$— is lower, which is disadvantageous for the development of a high clearing point of the liquid crystal mixture. The present inventors have found that the liquid crystal compounds containing a difluoromethyleneoxy group in which a alkyl chain or terminal alkyl chain is replaced by a cyclopentyl group, i.e., the present invention provides the formula I of compounds, increase the clearing point significantly, and their rotational viscosity is lower, as well as have a fast response speed. Also the synthesis of these compounds is simple and low cost. These compounds are very important practical significance for modulating liquid crystal mixture with low viscosity.

What is claimed is:

1. A compound of formula II:

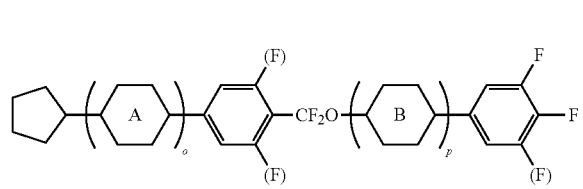

Formula II wherein

A is selected from at least one of 1,4-cyclohexylidene, 1,4-phenylene, and fluoro-substituted 1,4-phenylene, and B is selected from at least one of 1,4-phenylene, and fluoro-substituted 1,4-phenylene; p is 0 or 1; o is 1 or 2, and —(F) represents F or H.

2. The compound according to claim 1, wherein the compound of formula II is selected from at least one of formulas II1 to II13:

II1
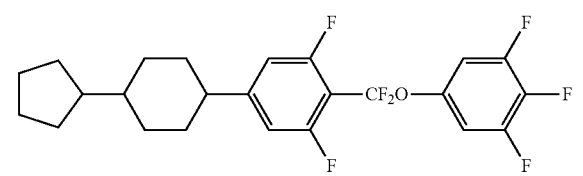

II2
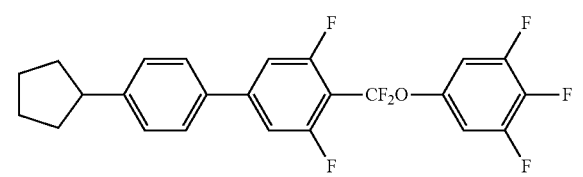

II3
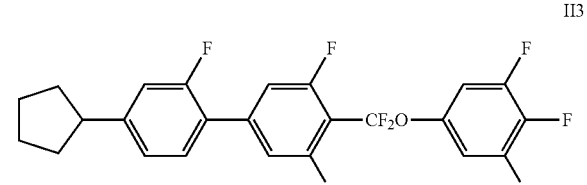

II4
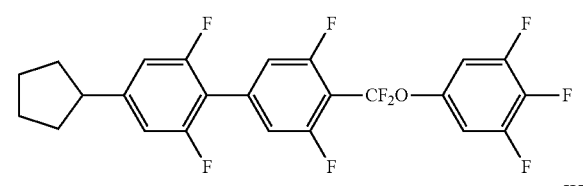

II5
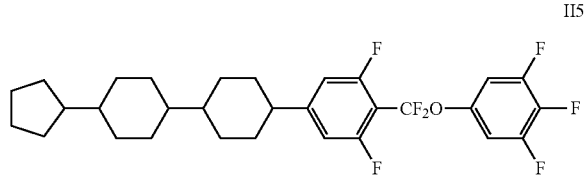

II6
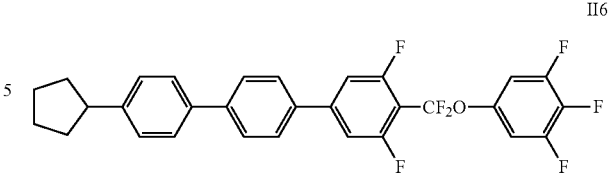

II7
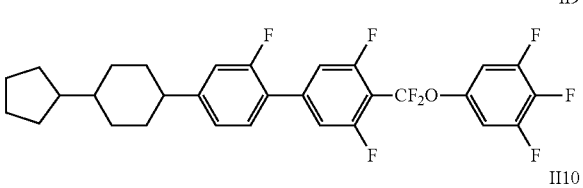

II8
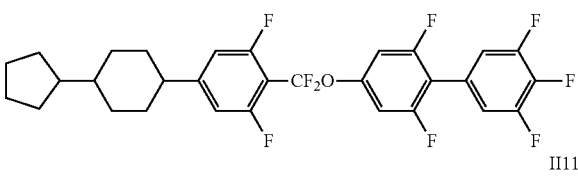

II9
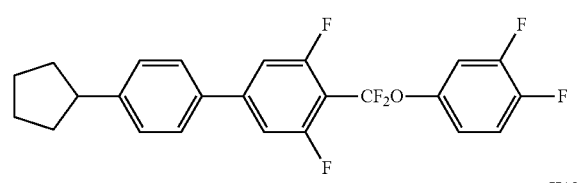

II10
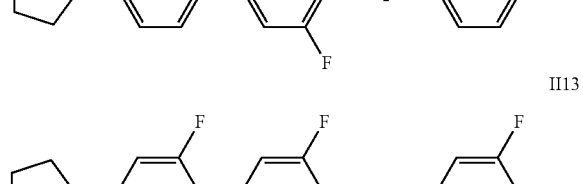

II11
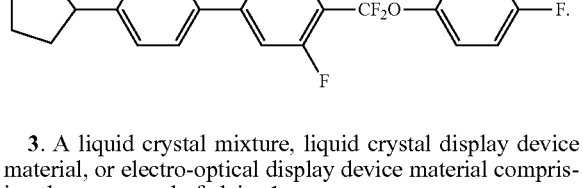

II12
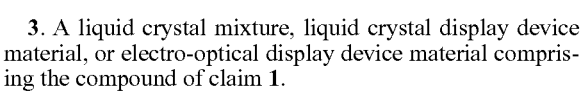

II13
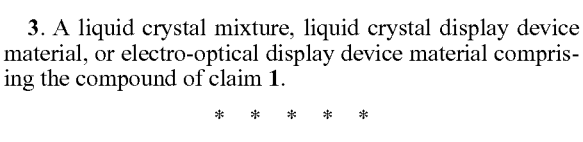

3. A liquid crystal mixture, liquid crystal display device material, or electro-optical display device material comprising the compound of claim 1.

* * * * *